US 11,400,054 B2

(12) United States Patent
Huang et al.

(10) Patent No.: US 11,400,054 B2
(45) Date of Patent: Aug. 2, 2022

(54) METHOD FOR TREATING AN AUTOIMMUNE NEUROLOGICAL DISEASE AND/OR NEURODEGENERATIVE DISEASE AND PHARMACEUTICAL FORMULATIONS FOR A LIQUID DOSAGE FORM AND A CONTROLLED RELEASE DOSAGE FORM

(71) Applicant: INDUSTRIAL TECHNOLOGY RESEARCH INSTITUTE, Hsinchu (TW)

(72) Inventors: Kuo-Kuei Huang, Zhubei (TW); I-Hong Pan, Zhubei (TW); Shu-Fang Wen, Baoshan Township (TW); Meng-Nan Lin, Zhubei (TW); I-Huang Lu, Hsinchu (TW); Zong-Keng Kuo, New Taipei (TW); Chu-Hsun Lu, Kaohsiung (TW); Tze-Chung Lee, Taoyuan (TW); Ya-Yan Yang, Wuci Township (TW); Jia-Horng Liaw, Taipei (TW); Pei-Hsin Lin, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 193 days.

(21) Appl. No.: 16/023,940

(22) Filed: Jun. 29, 2018

(65) Prior Publication Data
US 2019/0000776 A1 Jan. 3, 2019

Related U.S. Application Data

(60) Provisional application No. 62/527,300, filed on Jun. 30, 2017.

(51) Int. Cl.
*A61K 31/047* (2006.01)
*A61K 31/215* (2006.01)
(Continued)

(52) U.S. Cl.
CPC .......... *A61K 31/047* (2013.01); *A61K 9/0019* (2013.01); *A61K 9/08* (2013.01);
(Continued)

(58) Field of Classification Search
CPC .. A61K 31/047; A61K 31/215; A61K 31/335; A61K 9/5078; A61K 31/352; A61K 9/0019; A61K 31/045
See application file for complete search history.

(56) References Cited

U.S. PATENT DOCUMENTS 4,639,469 A 1/1987 Corvi-Mora
7,927,613 B2 4/2011 Almarsson et al.
(Continued)

FOREIGN PATENT DOCUMENTS

CN 105408320 A 3/2016
TW 201718017 A 6/2017
(Continued)

OTHER PUBLICATIONS

Muschert, S.. "Prediction of drug release from ethylcellulose coated pellets," Journal of Controlled Release, 2009, vol. 135, No. 1, pp. 71-79.
Taiwanese Office Action for Appl. No. 107122881 dated Aug. 29, 2019.
Torkildsen, O., et al, "Disease-modifying treatments for multiple sclerosis—a review of approved medications," European Journal of Neurology, 2015, vol. 23 (Suppl. 1), pp. 18-27.
Bellussi et al., "Evaluation of the efficacy and safety of sobrerol granules in patients suffering from chronic rhinosinusitis," Journal of International Medical Research, vol. 18, No. 6, Nov. 1, 1990, pp. 454-459, XP009507814.
(Continued)

*Primary Examiner* — Matthew P Coughlin
*Assistant Examiner* — Thurman Wheeler
(74) *Attorney, Agent, or Firm* — Birch, Stewart, Kolasch & Birch, LLP

(57) ABSTRACT

A method for treating an autoimmune neurological disease and/or a neurodegenerative disease is provided. The method includes administering an effective amount of at least one compound having Formula (I), Formula (II) or Formula (III), or its geometric isomer, enantiomer or diastereomer to a subject in need thereof:

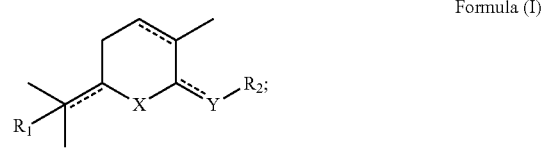

Formula (I)

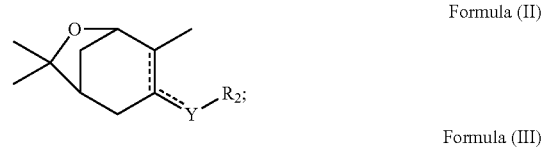

Formula (II)

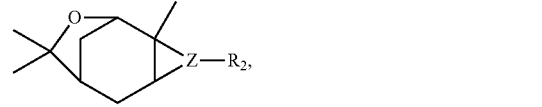

Formula (III)

wherein ══ is a single or double bond, X is $NCH_3$ or $CH_2$, Y is null, O or N, Z is O or N, $R_1$ is H, OH, and $R_2$ is null, H, $C_1$-$C_8$ alkyl, —(C═O)-alkyl, —(C═O)-aryl, —(C═O)-alkyl-aryl, —(C═O)-heteroaryl, cycloalkyl or heterocycloalkyl, which optionally substituted by one or more of —OH, —$NO_2$, —$NH_2$, —$NR_3R_4$, carbonyl, alkoxyl, alkyl or —$OCF_3$, wherein $R_3$ and $R_4$ independently are H, alkyl, —$SO_2CH_3$, —(C═O)—$CH_3$ or —(C═O)—$NH_2$.

9 Claims, 14 Drawing Sheets

(51) Int. Cl.
*A61K 31/335* (2006.01)
*A61K 9/50* (2006.01)
*A61K 31/352* (2006.01)
*A61K 9/00* (2006.01)
*A61K 31/045* (2006.01)
*A61P 37/00* (2006.01)
*A61P 25/28* (2006.01)
*A61K 9/08* (2006.01)
*A61K 9/14* (2006.01)
*A61K 31/075* (2006.01)
*A61K 31/122* (2006.01)
*A61K 31/222* (2006.01)
*A61K 31/343* (2006.01)
*A61K 47/02* (2006.01)
*A61K 47/26* (2006.01)
*A61K 47/34* (2017.01)
*A61K 47/38* (2006.01)
*A61K 47/40* (2006.01)

(52) U.S. Cl.
CPC ............ *A61K 9/146* (2013.01); *A61K 9/5078* (2013.01); *A61K 31/045* (2013.01); *A61K 31/075* (2013.01); *A61K 31/122* (2013.01); *A61K 31/215* (2013.01); *A61K 31/222* (2013.01); *A61K 31/335* (2013.01); *A61K 31/343* (2013.01); *A61K 31/352* (2013.01); *A61K 47/02* (2013.01); *A61K 47/26* (2013.01); *A61K 47/34* (2013.01); *A61K 47/38* (2013.01); *A61K 47/40* (2013.01); *A61P 25/28* (2018.01); *A61P 37/00* (2018.01)

(56) References Cited

U.S. PATENT DOCUMENTS

| 9,566,242 | B2 | 2/2017 | McDonnell et al. |
| 2003/0049256 | A1* | 3/2003 | Tobinick .............. A61K 9/0019 424/145.1 |
| 2004/0053888 | A1 | 3/2004 | Suzuki et al. |
| 2006/0109749 | A1 | 5/2006 | Terzian et al. |
| 2012/0213727 | A1 | 8/2012 | Hazan |
| 2013/0230587 | A1 | 9/2013 | Pilgaonkar et al. |
| 2017/0204422 | A1 | 7/2017 | Nelson et al. |

FOREIGN PATENT DOCUMENTS

| WO | WO 92/03128 A1 | 3/1992 |
| WO | WO 2017/043935 A1 | 3/2017 |

OTHER PUBLICATIONS

European Communication pursuant to Article 94(3) EPC for European Application No. 18739915.9, dated Jan. 22, 2021.
Giordano et al., "Interaction between trans-sobrerol enantiomers and β-cyclodextrin in aqueous solution and in the solid state," Bollettino Chimico Farmaceutico, vol. 129. No. 9, Sep. 1990, pp. 283-284, XP009507815.
Taiwanese Office Action and Search Report for Taiwanese Application No. 107122881, dated May 19, 2021.
Taiwanese Office Action for Appl. No. 107122881 dated Dec. 15, 2021.

* cited by examiner

METHOD FOR TREATING AN AUTOIMMUNE NEUROLOGICAL DISEASE AND/OR NEURODEGENERATIVE DISEASE AND PHARMACEUTICAL FORMULATIONS FOR A LIQUID DOSAGE FORM AND A CONTROLLED RELEASE DOSAGE FORM

CROSS REFERENCE TO RELATED APPLICATION

This application claims the benefit of U.S. Provisional Application No. 62/527,300, filed on Jun. 30, 2017, the entirety of which is incorporated by reference herein.

TECHNICAL FIELD

The technical field relates to a method for treating an autoimmune neurological disease and/or neurodegenerative disease and pharmaceutical formulations for a liquid dosage form and a controlled release dosage form.

BACKGROUND

Autoimmune diseases involving the central and peripheral nervous system are also known as autoimmune neurological diseases.

Multiple sclerosis (MS) is a disease that causes demyelination of spinal nerve and brain cells and is considered an autoimmune neurological disease. Patients with multiple sclerosis may experience a wide range of symptoms. Because of the nature of multiple sclerosis, symptoms can vary widely from person to person. The symptoms of multiple sclerosis may change in severity even from day to day, while the two most common symptoms are fatigue and difficulty walking.

Although multiple treatment options exist for autoimmune neurological diseases and/or neurodegenerative diseases, such as multiple sclerosis, no cure is yet available for them.

Therefore, there is need for a new therapy for autoimmune neurological diseases and/or neurodegenerative diseases.

SUMMARY

The present disclosure provides a method for treating an autoimmune neurological disease and/or a neurodegenerative disease. The method comprises administering an effective amount of at least one compound having Formula (I), Formula (II) or Formula (III), or its geometric isomer, enantiomer, diastereomer or pharmaceutically acceptable salt to a subject in need thereof.

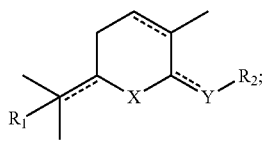

Formula (I)

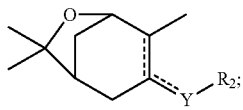

Formula (II)

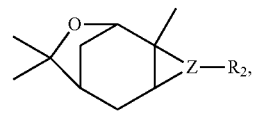

Formula (III)

wherein
═ is a single or double bond,
X is $NCH_3$ or $CH_2$,
Y is null, O or N,
Z is O or N,
$R_1$ is H, OH, and
$R_2$ is null, H, $C_1$-$C_8$ alkyl, —(C═O)-alkyl, —(C═O)-aryl, —(C═O)-alkyl-aryl, —(C═O)-heteroaryl, cycloalkyl or heterocycloalkyl, which optionally substituted by one or more of —OH, —$NO_2$, —$NH_2$, —$NR_3R_4$, carbonyl, alkoxyl, alkyl or —$OCF_3$, wherein $R_3$ and $R_4$ independently are H, alkyl, —$SO_2CH_3$, —(C═O)—$CH_3$ or —(C═O)—$NH_2$.

The present disclosure also provides a pharmaceutical formulation for a liquid dosage form of at least one compound having Formula (I), Formula (II) or Formula (III). The pharmaceutical formulation for a liquid dosage of at least one compound having Formula (I), Formula (II) or Formula (III) comprises: 0.1-30% by weight of at least one compound having Formula (I), Formula (II) or Formula (III), or its geometric isomer, enantiomer, diastereomer or pharmaceutically acceptable salt:

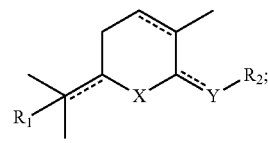

Formula (I)

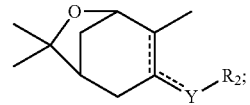

Formula (II)

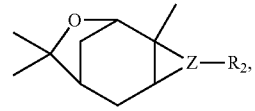

Formula (III)

wherein
═ is a single or double bond,
X is $NCH_3$ or $CH_2$,
Y is null, O or N,
Z is O or N,
$R_1$ is H, OH, and
$R_2$ is null, H, $C_1$-$C_8$ alkyl, —(C═O)-alkyl, —(C═O)-aryl, —(C═O)-alkyl-aryl, —(C═O)-heteroaryl, cycloalkyl or heterocycloalkyl, which optionally substituted by one or more of —OH, —$NO_2$, —$NH_2$, —$NR_3R_4$, carbonyl, alkoxyl, alkyl or —$OCF_3$, wherein $R_3$ and $R_4$ independently are H, alkyl, —$SO_2CH_3$, —(C═O)—$CH_3$ or —(C═O)—$NH_2$; and 0.1-15% by weight of a copolymer of poly(ethylene oxide) and poly(propylene oxide); 0.1-60% by weight of cyclodextrin or a derivative thereof; and 1-99% by weight of solvent.

The present disclosure further provides a pharmaceutical formulation for a controlled release dosage form of at least one compound having Formula (I), Formula (II) or Formula (III). The pharmaceutical formulation for a controlled release dosage form of at least one compound having Formula (I), Formula (II) or Formula (III) comprises:

a composition of a particle carrier;
a composition of a drug layer coated on the carrier, which comprises:
   at least one compound having Formula (I), Formula (II) or Formula (III), or its geometric isomer, enantiomer, diastereomer or pharmaceutically acceptable salt:

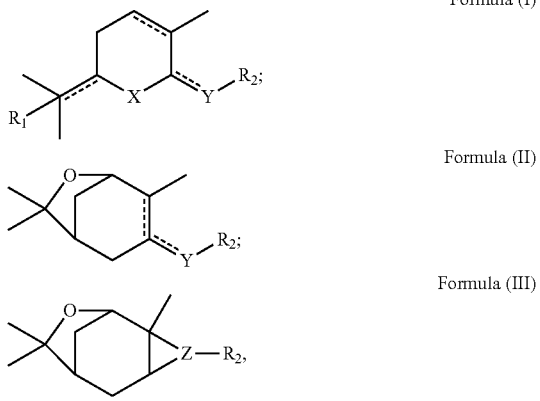

Formula (I)

Formula (II)

Formula (III)

wherein
── is a single or double bond,
X is $NCH_3$ or $CH_2$,
Y is null, O or N,
Z is O or N,
$R_1$ is H, OH, and
$R_2$ is null, H, $C_1$-$C_8$ alkyl, —(C═O)-alkyl, —(C═O)-aryl, —(C═O)-alkyl-aryl, —(C═O)-heteroaryl, cycloalkyl or heterocycloalkyl, which optionally substituted by one or more of —OH, —$NO_2$, —$NH_2$, —$NR_3R_4$, carbonyl, alkoxyl, alkyl or —$OCF_3$, wherein $R_3$ and $R_4$ independently are H, alkyl, —$SO_2CH_3$, —(C═O)—$CH_3$ or —(C═O)—$NH_2$; and
   at least one binder;
a composition of a controlled release layer coated on the drug layer; and
a composition of a coating layer coated on the drug layer, wherein in the pharmaceutical formulation for a controlled release dosage form, the composition of a particle carrier occupies 35-98% by weight, the composition of a drug layer occupies 1-64% by weight, and the composition of a controlled release layer occupies 0.5-50% by weight, and wherein the at least one compound having Formula (I), Formula (II) or Formula (III), or its geometric isomer, enantiomer, diastereomer or pharmaceutically acceptable salt occupies 1-99% by weight of the composition of a drug layer.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1:
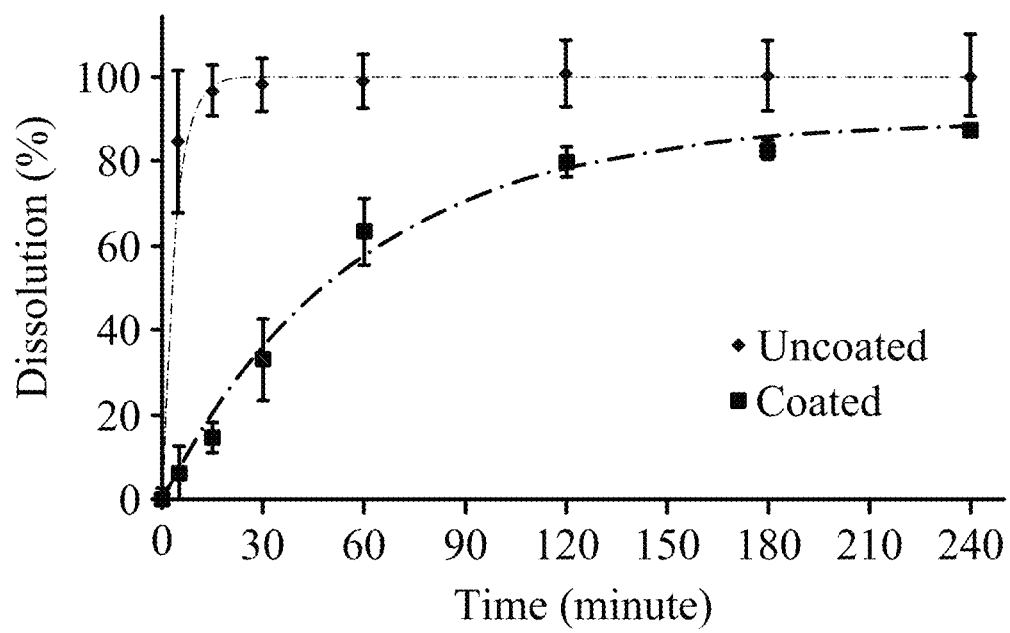
FIG. 1 shows the results of the dissolution testing for controlled release particles with 17% (−)trans-sobrerol (coated-drug carrying particles) and trans-sobrerol drug carrying-particles (uncoated-drug carrying particles)

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a method for treating an autoimmune neurological disease and/or a neurodegenerative disease. The method for treating an autoimmune neurological disease and/or a neurodegenerative disease may comprise, but is not limited to, administering an effective amount of at least one compound having Formula (I), Formula (II) or Formula (III), or its geometric isomer, enantiomer, diastereomer or pharmaceutically acceptable salt to a subject in need thereof:

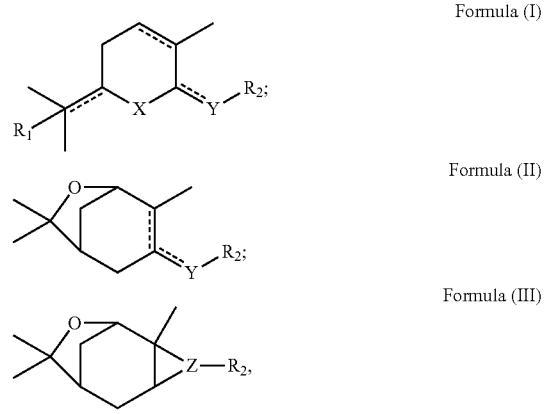

wherein
═══ may be a single or double bond,
X may be $NCH_3$ or $CH_2$,
Y may be null, O or N,
Z may be O or N,
$R_1$ may be H, OH, and
$R_2$ may be null, H, $C_1$-$C_8$ alkyl, —(C═O)-alkyl, —(C═O)-aryl, —(C═O)-alkyl-aryl, —(C═O)-heteroaryl, cycloalkyl or heterocycloalkyl, which optionally substituted by one or more of —OH, —$NO_2$, —$NH_2$, —$NR_3R_4$, carbonyl, alkoxyl, alkyl or —$OCF_3$, wherein $R_3$ and $R_4$ independently are H, alkyl, —$SO_2CH_3$, —(C═O)—$CH_3$ or —(C═O)—$NH_2$.

In one embodiment, in the above Formula (I), Formula (II) or Formula (III), X may be $NCH_3$ or $CH_2$, Y may be null, O or N, $R_1$ may be H, OH, and $R_2$ may be null, H, Me, $C_2H_5$, $C_3H_7$, $C_4H_9$, $C_7H_7$, $COCH_3$, $COC_2H_5$, $COC_3H_7$, $COC_4H_9$, $COC_5H_{11}$, $COC_6H_5$, $COCH_2C_6H_5$, $COC_2H_4C_6H_5$, $COC_6H_4NO_2$, or $COC_6H_4OH$, but they are not limited thereto.

The autoimmune neurological diseases mentioned above may comprise multiple sclerosis, Neuromyelitis optica, Lambert-Eaton myasthenic syndrome, autoimmune inner ear disease, narcolepsy, neuromyotonia, Guillain-Barre syndrome, myasthenia gravis, systemic lupus erythematosus, transverse myelitis or acute disseminated encephalomyelitis, but it is not limited thereto. Moreover, examples of the neurodegenerative diseases mentioned above may comprise, but are not limited to Alzheimer's disease, Huntington's disease, Parkinson's disease, Schizophrenia, depression, Amyotrophic lateral sclerosis, multi-infarct dementia, motor neuron disease or neurofibromatosis, but it is not limited thereto. In one embodiment, the autoimmune neurological disease and/or neurodegenerative disease mentioned above may be multiple sclerosis (MS).

The term "an effective amount" used herein means an amount of a compound or a drug which will have a therapeutic effect, or an amount of a compound or a drug that is sufficient to achieve the desired clinical improvement.

Examples of a compound having Formula (I) shown above may comprise compounds having any one of Formula (IV) to Formula (XVI), but they are not limited thereto:

Formula (IV)
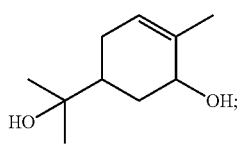

Formula (V)
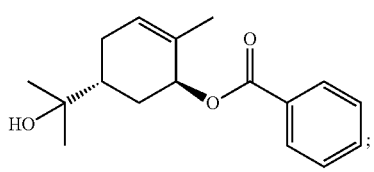

Formula (VI)
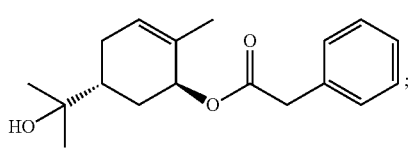

Formula (VII)
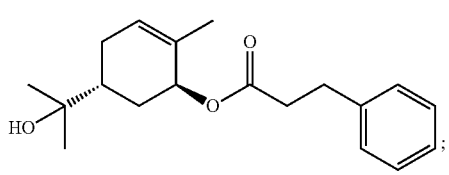

Formula (VIII)
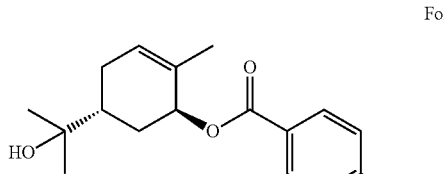

Formula (IX)
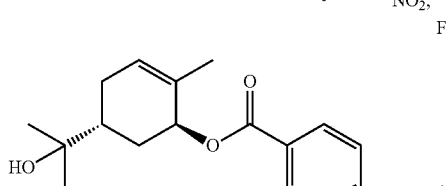

Formula (X)
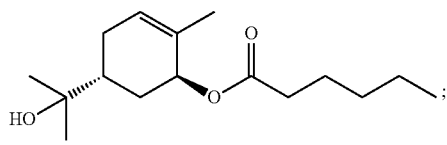

Formula (XI)
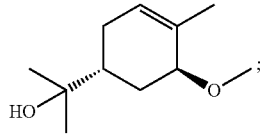

Formula (XII)
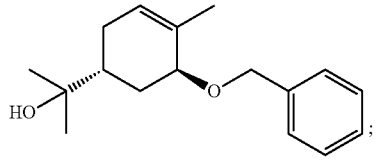

Formula (XIII)
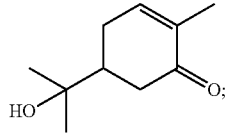

Formula (XIV)
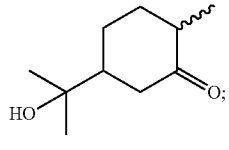

Formula (XV)
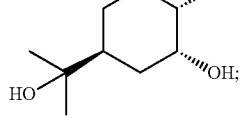

Formula (XVI)
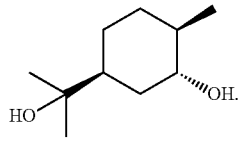

Furthermore, examples of a compound having Formula (II) shown above may comprise compounds having Formula (XVII), but they are not limited thereto:

Formula (XVII)

In addition, examples of a compound having Formula (III) shown above may comprise compounds having Formula (XVIII), but they are not limited thereto:

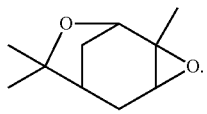

Formula (XVIII)

In one embodiment, for the method for treating an autoimmune neurological disease and/or a neurodegenerative disease, the at least one compound having Formula (I), Formula (II) or Formula (III), or its geometric isomer, enantiomer, diastereomer or pharmaceutically acceptable salt mentioned above may be at least one compound having Formula (IV), and may be sobrerol. The sobrerol may comprise, but is not limited to, (+) trans-sobrerol, (−) trans-sobrerol, (+) cis-sobrerol, (−) cis-sobrerol or a combination thereof.

In the foregoing embodiment in which the at least one compound having Formula (I), Formula (II) or Formula (III), or its geometric isomer, enantiomer, diastereomer or pharmaceutically acceptable salt mentioned above may be at least one compound having Formula (IV) shown above, and may be sobrerol, for one specific embodiment, the sobrerol may be (+) trans-sobrerol, for another specific embodiment, the sobrerol may be (−) trans-sobrerol, and for yet another specific embodiment, the sobrerol may be a mixture of (+) trans-sobrerol and (−) trans-sobrerol.

For the method for treating an autoimmune neurological disease and/or a neurodegenerative disease, in the foregoing embodiment in which the at least one compound having Formula (I), Formula (II) or Formula (III), or its geometric isomer, enantiomer, diastereomer or pharmaceutically acceptable salt mentioned above may be at least one compound having Formula (IV), and may be sobrerol, the autoimmune neurological disease and/or a neurodegenerative disease may be multiple sclerosis, but it is not limited thereto.

In another embodiment, for the method for treating an autoimmune neurological disease and/or a neurodegenerative disease, the at least one compound having Formula (I), Formula (II) or Formula (III), or its geometric isomer, enantiomer, diastereomer or pharmaceutically acceptable salt mentioned above may have any one of Formula (V) to Formula (XVIII) shown above. In one specific embodiment, for the method for treating an autoimmune neurological disease and/or a neurodegenerative disease, the at least one compound having Formula (I), Formula (II) or Formula (III), or its geometric isomer, enantiomer, diastereomer or pharmaceutically acceptable salt mentioned above may be at least one compound having Formula (I) and have any one of Formula (V) to Formula (XVI) shown above. In another specific embodiment, for the method for treating an autoimmune neurological disease and/or a neurodegenerative disease, the at least one compound having Formula (I), Formula (II) or Formula (III), or its geometric isomer, enantiomer, diastereomer or pharmaceutically acceptable salt mentioned above may be at least one compound having Formula (II) and have Formula (XVII) shown above. In yet another specific embodiment, for the method for treating an autoimmune neurological disease and/or a neurodegenerative disease, the at least one compound having Formula (I), Formula (II) or Formula (III), or its geometric isomer, enantiomer, diastereomer or pharmaceutically acceptable salt mentioned above may be at least one compound having Formula (III) and have Formula (XVIII) shown above.

In any of the above-mentioned methods for treating an autoimmune neurological disease and/or a neurodegenerative disease, the subject may include, but is not limited to, a vertebrate. Moreover, the vertebrate mentioned above may include a fish, an amphibian, a reptile, a bird, or a mammal, but it is not limited thereto. Examples of mammals include, but are not limited to, a human, an orangutan, a monkey, a horse, a donkey, a dog, a cat, a rabbit, a guinea pig, a rat, and a mouse. In one embodiment, in any of the above-mentioned methods for treating an autoimmune neurological disease and/or a neurodegenerative disease of the present disclosure, the subject is a human.

Furthermore, the present disclosure also provides a novel pharmaceutical formulation for a liquid dosage form of at least one compound having Formula (I) or Formula (II).

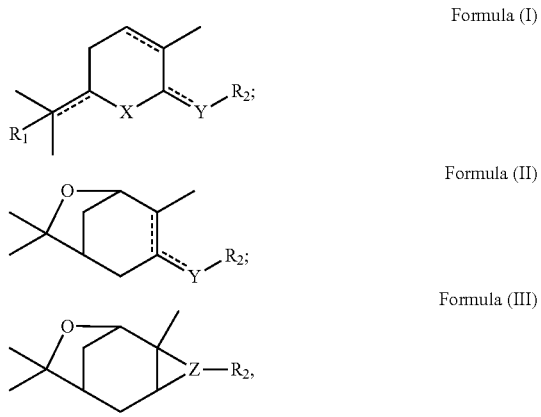

Formula (I)

Formula (II)

Formula (III)

wherein

⸺ may be a single or double bond,

X may be $NCH_3$ or $CH_2$,

Y may be null, O or N,

Z may be O or N, $R_1$ may be H, OH, and $R_2$ may be null, H, $C_1$-$C_8$ alkyl, —(C═O)-alkyl, —(C═O)-aryl, —(C═O)-alkyl-aryl, —(C═O)-heteroaryl, cycloalkyl or heterocycloalkyl, which optionally substituted by one or more of —OH, —$NO_2$, —$NH_2$, —$NR_3R_4$, carbonyl, alkoxyl, alkyl or —$OCF_3$, wherein $R_3$ and $R_4$ independently are H, alkyl, —$SO_2CH_3$, —(C═O)—$CH_3$ or —(C═O)—$NH_2$.

In one embodiment, in the above Formula (I), Formula (II) or Formula (III), X may be $NCH_3$ or $CH_2$, Y may be null, O or N, $R_1$ may be H, OH, and $R_2$ may be null, H, Me, $C_2H_5$, $C_3H_7$, $C_4H_9$, $C_7H_7$, $COCH_3$, $COC_2H_5$, $COC_3H_7$, $COC_4H_9$, $COC_5H_{11}$, $COC_6H_5$, $COCH_2C_6H_5$, $COC_2H_4C_6H_5$, $COC_6H_4NO_2$, or $COC_6H_4OH$, but they are not limited thereto.

The foregoing pharmaceutical formulation for a liquid dosage of at least one compound having Formula (I), Formula (II) or Formula (III) shown above may comprise, but is not limited to, at least one compound having Formula (I), Formula (II) or Formula (III), or its geometric isomer, enantiomer, diastereomer or pharmaceutically acceptable salt, a copolymer of poly(ethylene oxide) and poly(propylene oxide), cyclodextrin or a derivative thereof and a solvent.

In the pharmaceutical formulation for a liquid dosage form of at least one compound having Formula (I), Formula (II) or Formula (III) of the present disclosure mentioned above, the at least one compound having Formula (I), Formula (II) or Formula (III), or its geometric isomer, enantiomer, diastereomer or pharmaceutically acceptable salt may occupy about 0.1-30% by weight, such as about 0.1-10%, about 5-25%, about 10-20% or about 20-30% by weight, but it is not limited thereto.

Examples of a compound having Formula (I) may be the same as those recited in the paragraphs above related to the method for treating an autoimmune neurological disease and/or a neurodegenerative disease of the present disclosure, and are not repeated herein to avoid redundancy.

Similarly, examples of a compound having Formula (II) and examples of a compound having Formula (III) may be the same as those recited in the paragraphs above related to the method for treating an autoimmune neurological disease and/or a neurodegenerative disease of the present disclosure, and are not repeated herein to avoid redundancy.

Moreover, in the pharmaceutical formulation for a liquid dosage form of at least one compound having Formula (I) or Formula (II) of the present disclosure mentioned above, the copolymer of poly(ethylene oxide) and poly(propylene oxide) may occupy about 0.1-15% by weight, such as about 0.1-5%, about 0.5-12%, about 5-10% or about 10-15% by weight, but it is not limited thereto.

Examples of the copolymer of poly(ethylene oxide) and poly(propylene oxide) may comprise, but are not limited to poly(ethylene oxide)x-poly(propylene oxide)y-poly(ethylene oxide)x (PEO-PPO-PEO). For the poly(ethylene oxide)x-poly(propylene oxide)y-poly(ethylene oxide)x, x may be an integer of about 30-120, such as about 30-60, about 40-100, about 60-120 while y may be an integer of about 10-50, such as about 10-25, about 20-40, about 25-50, but they are not limited thereto.

Furthermore, in the pharmaceutical formulation for a liquid dosage form of at least one compound having Formula (I), Formula (II) or Formula (III) of the present disclosure mentioned above, the cyclodextrin or a derivative thereof may occupy about 0.1-60% by weight, such as about 0.1-20%, about 1-50%, about 5-40%, about 20-40% or about 40-60% by weight, but it is not limited thereto.

The derivative of cyclodextrin may comprise 2-hydroxypropyl-beta cyclodextrin, 2-hydroxypropyl-γ-cyclodextrin, β-CD sulfobutyl ether sodium salt or randomly methylated β-cyclodextrin, etc., but it is not limited thereto.

In addition, in the pharmaceutical formulation for a liquid dosage form of at least one compound having Formula (I), Formula (II) or Formula (III) of the present disclosure mentioned above, the solvent may occupy about 1-99% by weight, such as about 1-30%, about 10-85%, about 20-70%, about 30-60% or about 60-99% by weight, but it is not limited thereto.

The solvent suitable for the pharmaceutical formulation for a liquid dosage form of at least one compound having Formula (I), Formula (II) or Formula (III) of the present disclosure may comprise, but is not limited to, water, ethanol, etc.

In one embodiment, in the pharmaceutical formulation for a liquid dosage form of at least one compound having Formula (I), Formula (II) or Formula (III) of the present disclosure mentioned above, the at least one compound having Formula (I), Formula (II) or Formula (III), or its geometric isomer, enantiomer, diastereomer or pharmaceutically acceptable salt may occupy about 0.1-30% by weight, the copolymer of poly(ethylene oxide) and poly(propylene oxide) may occupy about 0.1-15% by weight, the cyclodextrin or a derivative thereof may occupy about 0.1-60% by weight, and the solvent may occupy about 1-99% by weight.

Moreover, in one embodiment, in the pharmaceutical formulation for a liquid dosage form of at least one compound having Formula (I), Formula (II) or Formula (III) of the present disclosure mentioned above, the at least one compound having Formula (I), Formula (II) or Formula (III), or its geometric isomer, enantiomer, diastereomer or pharmaceutically acceptable salt may occupy about 0.1-30% by weight, the copolymer of poly(ethylene oxide) and poly(propylene oxide) may occupy about 0.1-15% by weight, the cyclodextrin or a derivative thereof may occupy about 0.1-60% by weight, and the solvent may occupy about 1-99% by weight, wherein the copolymer of poly(ethylene oxide) and poly(propylene oxide) may be poly(ethylene oxide)x-poly(propylene oxide)y-poly(ethylene oxide)x, in which, x is an integer of 76 and y is an integer of 30, and wherein the cyclodextrin or derivative thereof may be 2-hydroxypropyl-beta cyclodextrin. For this embodiment, the at least one compound having Formula (I), Formula (II) or Formula (III) may have Formula (IV), and may be sobrerol, but it is not limited thereto.

Furthermore, in the embodiment mentioned above, the foregoing sobrerol may comprise (+) trans-sobrerol, (−) trans-sobrerol, (+) cis-sobrerol, (−) cis-sobrerol, or a combination thereof, but it is not limited thereto. In one specific embodiment, the sobrerol is (+) trans-sobrerol. In another specific embodiment, the sobrerol is (−) trans-sobrerol. In yet another embodiment, the sobrerol is a mixture of (+) trans-sobrerol and (−) trans-sobrerol.

In another embodiment, for the pharmaceutical formulation for a liquid dosage form of at least one compound having Formula (I), Formula (II) or Formula (III) of the present disclosure, the at least one compound having Formula (I), Formula (II) or Formula (III), or its geometric isomer, enantiomer, diastereomer or pharmaceutically acceptable salt mentioned above may have any one of Formula (V) to Formula (XVIII) shown above. In one specific embodiment, for the pharmaceutical formulation for a liquid dosage form of at least one compound having Formula (I), Formula (II) or Formula (III) of the present disclosure, the at least one compound having Formula (I), Formula (II) or Formula (III), or its geometric isomer, enantiomer, diastereomer or pharmaceutically acceptable salt mentioned above may be at least one compound having Formula (I) and have any one of Formula (V) to Formula (XVI) shown above. In another specific embodiment, for the pharmaceutical formulation for a liquid dosage form of at least one compound having Formula (I), Formula (II) or Formula (III) of the present disclosure, the at least one compound having Formula (I), Formula (II) or Formula (III), or its geometric isomer, enantiomer, diastereomer or pharmaceutically acceptable salt mentioned above may be at least one compound having Formula (II) and have Formula (XVII) shown above. In yet another specific embodiment, for the pharmaceutical formulation for a liquid dosage form of at least one compound having Formula (I), Formula (II) or Formula (III) of the present disclosure, the at least one compound having Formula (I), Formula (II) or Formula (III), or its geometric isomer, enantiomer, diastereomer or pharmaceutically acceptable salt mentioned above may be at least one compound having Formula (III) and have Formula (XVIII) shown above.

Any foregoing pharmaceutical formulation for a liquid dosage form of at least one compound having Formula (I), Formula (II) or Formula (III) is capable of decreasing a dosage and/or dosing frequency to a subject in need of being administered at least one compound having Formula (I), Formula (II) or Formula (III), or its geometric isomer, enantiomer, diastereomer or pharmaceutically acceptable salt.

The subject in need of being administered at least one compound having Formula (I), Formula (II) or Formula (III), or its geometric isomer, enantiomer, diastereomer or pharmaceutically acceptable salt may comprise a subject suffering from a disease which can be treated by at least one compound having Formula (I), Formula (II) or Formula (III), or its geometric isomer, enantiomer, diastereomer or pharmaceutically acceptable salt, but it is not limited thereto. In one embodiment, the disease may comprise, but is not limited to, an autoimmune neurological disease and/or a neurodegenerative disease. In one specific embodiment, the disease may be multiple sclerosis.

In addition, the foregoing subject may include, but is not limited to, a vertebrate. The vertebrate mentioned above may include a fish, an amphibian, a reptile, a bird, or a mammal, but it is not limited thereto. Examples of mammals include, but are not limited to, a human, an orangutan, a monkey, a horse, a donkey, a dog, a cat, a rabbit, a guinea pig, a rat, and a mouse. In one embodiment, the subject is a human.

Also, the present disclosure further provides a novel pharmaceutical formulation for a controlled release dosage form of at least one compound having Formula (I), Formula (II) or Formula (III) shown in the following.

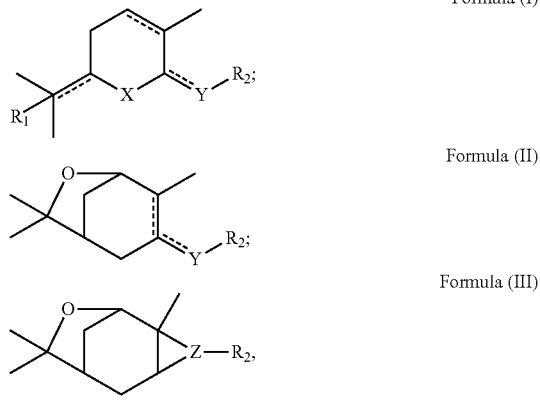

Formula (I)

Formula (II)

Formula (III)

wherein
___ may be a single or double bond,
X may be $NCH_3$ or $CH_2$,
Y may be null, O or N,
Z may be O or N,
$R_1$ may be H, OH, and
$R_2$ may be null, H, $C_1$-$C_8$ alkyl, —(C=O)-alkyl, —(C=O)-aryl, —(C=O)-alkyl-aryl, —(C=O)-heteroaryl, cycloalkyl or heterocycloalkyl, which optionally substituted by one or more of —OH, —$NO_2$, —$NH_2$, —$NR_3R_4$, carbonyl, alkoxyl, alkyl or —$OCF_3$, wherein $R_3$ and $R_4$ independently are H, alkyl, —$SO_2CH_3$, —(C=O)—$CH_3$ or —(C=O)—$NH_2$.

In one embodiment, in the above Formula (I), Formula (II) or Formula (III), X may be $NCH_3$ or $CH_2$, Y may be null, O or N, $R_1$ may be H, OH, and $R_2$ may be null, H, Me, $C_2H_5$, $C_3H_7$, $C_4H_9$, $C_7H_7$, $COCH_3$, $COC_2H_5$, $COC_3H_7$, $COC_4H_9$, $COC_5H_{11}$, $COC_6H_5$, $COCH_2C_6H_5$, $COC_2H_4C_6H_5$, $COC_6H_4NO_2$, or $COC_6H_4OH$, but they are not limited thereto.

The foregoing pharmaceutical formulation for a controlled release dosage form of at least one compound having Formula (I), Formula (II) or Formula (III) shown above may comprise a composition of a particle carrier, a composition of a drug layer comprising at least one compound having Formula (I), Formula (II) or Formula (III), or its geometric isomer, enantiomer, diastereomer or pharmaceutically acceptable salt and at least one binder, and a composition of a controlled release layer, but it is not limited thereto. For the controlled release dosage form of at least one compound having Formula (I), Formula (II) or Formula (III) mentioned above, the drug layer is coated on the particle carrier while the controlled release layer is coated on the drug layer.

In the pharmaceutical formulation for a controlled release dosage form of at least one compound having Formula (I), Formula (II) or Formula (III) of the present disclosure mentioned above, the composition of a particle carrier may occupy about 35-98% by weight, such as about 30-60%, about 40-90%, about 35-95%, about 50-85% by weight, but it is not limited thereto.

The composition of a particle carrier mentioned above may comprise microcrystalline cellulose, lactose, corn starch, mannitol, sodium carboxymethyl cellulose, common salt, germanium dioxide, combinations thereof, etc., but it is not limited thereto. The particle size of the particle carrier may be about 100-1300 μm, such as about 200-1000 μm, about 500-710 μm, but it is not limited thereto.

Moreover, in the pharmaceutical formulation for a controlled release dosage form of at least one compound having Formula (I), Formula (II) or Formula (III) of the present disclosure mentioned above, the composition of a drug layer may occupy about 1-64% by weight, such as about 5-60%, about 15-50%, about 8-32 by weight, but it is not limited thereto. Furthermore, the at least one compound having Formula (I), Formula (II) or Formula (III), or its geometric isomer, enantiomer, diastereomer or pharmaceutically acceptable salt may occupy 1-99% by weight, such as about 5-50%, about 20-80%, about 40-90% by weight of the foregoing composition of a drug layer.

Examples of a compound having Formula (I) may be the same as those recited in the paragraphs above related to the method for treating an autoimmune neurological disease and/or a neurodegenerative disease of the present disclosure, and are not repeated herein to avoid redundancy.

Similarly, examples of a compound having Formula (II) may be the same as those recited in the paragraphs above related to the method for treating an autoimmune neurological disease and/or a neurodegenerative disease of the present disclosure, and are not repeated herein to avoid redundancy.

The least one binder in the composition of a drug layer mentioned above may comprise hydroxypropyl methyl cellulose, hydroxypropyl cellulose, polyvinyl, polyvinyl alcohol or a combination thereof, but it is not limited thereto.

In one embodiment, for the pharmaceutical formulation for a controlled release dosage form of at least one compound having Formula (I) or Formula (II) of the present disclosure, the composition of a drug layer mentioned above may further comprise, but is not limited to, an anti-adherent, a plasticizer, another excipient, or a combination thereof.

Examples of the anti-adherent suitable for the composition of a drug layer mentioned above may comprise, but is not limited to, talc powder, stearic acid, stearate or colloidal silicon dioxide, but they are not limited thereto.

The plasticizer suitable for the composition of a drug layer mentioned above may comprise triethyl citrate, tributyl citrate, polyethylene glycol, etc., but it is not limited thereto.

Other excipients suitable for the composition of a drug layer mentioned above may comprise, but are not limited to lactose, starch, mannitol, pigments, microcrystalline cellulose, castor oil, etc.

In the composition of a drug layer mentioned above, the content of the at least binder, the content of the anti-adherent, the content of the plasticizer and/or the contents of other excipients have no specific limitations, and can be adjusted according the content of the least one compound having Formula (I), Formula (II) or Formula (III), or its geometric isomer, enantiomer, diastereomer or pharmaceutically acceptable salt and/or can be adjusted as needed.

Furthermore, the composition of a controlled release layer mentioned above may comprise at least one water-insoluble polymer or wax-like ingredient, but it is not limited thereto. Moreover, in the pharmaceutical formulation for a controlled release dosage form of at least one compound having Formula (I), Formula (II) or Formula (III) of the present disclosure mentioned above, the composition of a controlled release layer may occupy about 0.5-50% by weight, such as about 1-50%, about 0.5-20%, about 5-40 by weight, but it is not limited thereto.

The at least one water-insoluble polymer or wax-like ingredient mentioned above may comprise, but is not limited to ethyl cellulose, hydroxypropyl cellulose, hydroxypropyl methyl cellulose, ethyl acrylate-methyl methacrylate-trimethyl ammonium chloride ethyl methacrylate copolymer, methyl methacrylate-ethyl acrylate copolymer, polyvinylpyrrlidone, polyvinyl alcohol, hydrogenated castor oil, hydrogenated coconut oil, stearic acid, stearyl alcohol or a combination thereof.

In one embodiment, for the pharmaceutical formulation for a controlled release dosage form of at least one compound having Formula (I), Formula (II) or Formula (III) of the present disclosure, the composition of a controlled release layer mentioned above may further comprise an anti-adherent, a plasticizer, other excipients or a combination thereof, but it is not limited thereto.

The anti-adherent suitable for the composition of a controlled release layer mentioned above may comprise, but is not limited to, talc powder, stearic acid, stearate or colloidal silicon dioxide.

The plasticizer suitable for the composition of a controlled release layer mentioned above may comprise triethyl citrate, tributyl citrate, polyethylene glycol, etc., but it is not limited thereto.

Other excipients suitable for the composition of a controlled release layer mentioned above may comprise, but are not limited to lactose, starch, mannitol, pigments, microcrystalline cellulose, castor oil, etc.

In the composition of a controlled release layer mentioned above, the content of the anti-adherent, the content of the plasticizer and/or the content of other excipients has no specific limitations, and can be adjusted according the content of at least one water-insoluble polymer and/or can be adjusted as needed.

In one embodiment, for the pharmaceutical formulation for a controlled release dosage form of at least one compound having Formula (I), Formula (II) or Formula (III) of the present disclosure, the composition of a particle carrier may occupy about 35-98% by weight, the composition of a drug layer may occupy about 1-64% by weight, and the composition of a controlled release layer may occupy about 0.5-50% by weight, wherein the at least one compound having Formula (I), Formula (II) or Formula (III), or its geometric isomer, enantiomer, diastereomer or pharmaceutically acceptable salt may occupy about 1-99% by weight of the composition of a drug layer. For this embodiment, the at least one compound having Formula (I), Formula (II) or Formula (III) may have Formula (IV), and may be sobrerol, but it is not limited thereto.

Moreover, in this embodiment, the foregoing sobrerol may comprise (+) trans-sobrerol, (−) trans-sobrerol, (+) cis-sobrerol, (−) cis-sobrerol, or a combination thereof, but it is not limited thereto. In one specific embodiment, the sobrerol is (+) trans-sobrerol. In another specific embodiment, the sobrerol is (−) trans-sobrerol. In yet another embodiment, the sobrerol is a mixture of (+) trans-sobrerol and (−) trans-sobrerol.

Alternatively, in this embodiment, the composition of a particle carrier may comprise microcrystalline cellulose, the composition of a drug layer may comprise (−) trans-sobrerol, at least one binder comprising hydroxypropyl methyl cellulose, and an anti-adherent comprising talcum powder, and the composition of a controlled release layer may comprise at least one water-insoluble polymer comprising ethyl cellulose and hydroxypropyl methyl cellulose, and an anti-adherent comprising talcum powder. Moreover, the composition of a particle carrier may occupy about 40-90% by weight, the composition of a drug layer may occupy about 15-50% by weight, and the composition of a controlled release layer may occupy about 1-15% by weight, and the (−) trans-sobrerol may occupy about 40-90% by weight of the composition of a drug layer.

Or, in this embodiment, the composition of a particle carrier may comprise microcrystalline cellulose, the composition of a drug layer comprises (−) trans-sobrerol and at least one binder comprising polyvinyl pyrrolidone, the composition of a controlled release layer comprises at least one water-insoluble polymer comprising ethyl cellulose and hydroxypropyl methyl cellulose. In addition, the composition of a particle carrier may occupy about 5-60% by weight, the composition of a drug layer may occupy about 35-95% by weight, and the composition of a controlled release layer may occupy about 0.5-20% by weight, wherein the (−) trans-sobrerol may occupy about 40-90% by weight of the composition of a drug layer.

Or, in this embodiment, the composition of a particle carrier may comprise microcrystalline cellulose, the composition of a drug layer may comprise a mixture of (+) trans-sobrerol and (−) trans-sobrerol and at least one binder comprising polyvinyl pyrrolidone, the composition of a controlled release layer may comprise at least one water-insoluble polymer comprising ethyl cellulose and hydroxypropyl methyl cellulose. In addition, the composition of a particle carrier may occupy about 35-95% by weight, the composition of a drug layer may occupy about 5-60% by weight, and the composition of a controlled release layer may occupy about 0.5-20% by weight, wherein the mixture of (+) trans-sobrerol and (−) trans-sobrerol may occupy about 40-90% by weight of the composition of a drug layer.

In addition, in another embodiment, for the pharmaceutical formulation for a controlled release dosage form of at least one compound having Formula (I), Formula (II) or Formula (III), the at least one compound having Formula (I), Formula (II) or Formula (III), or its geometric isomer, enantiomer, diastereomer or pharmaceutically acceptable salt mentioned above may have any one of Formula (V) to Formula (XVIII) shown above. In one specific embodiment, for the pharmaceutical formulation for a controlled release dosage form of at least one compound having Formula (I), Formula (II) or Formula (III), the at least one compound having Formula (I), Formula (II) or Formula (III), or its geometric isomer, enantiomer, diastereomer or pharmaceutically acceptable salt mentioned above may be at least one compound having Formula (I) and have any one of Formula (V) to Formula (XVI) shown above. In another specific embodiment, for the pharmaceutical formulation for a controlled release dosage form of at least one compound having Formula (I), Formula (II) or Formula (III), the at least one compound having Formula (I), Formula (II) or Formula (III), or its geometric isomer, enantiomer, diastereomer or pharmaceutically acceptable salt mentioned above may be at least one compound having Formula (II) and have Formula (XVII) shown above. In yet another specific embodiment, for the pharmaceutical formulation for a controlled release dosage form of at least one compound having Formula (I), Formula (II) or Formula (III), the at least one compound having Formula (I), Formula (II) or Formula (III), or its geometric isomer, enantiomer, diastereomer or pharmaceutically acceptable salt mentioned above may be at least one compound having Formula (III) and have Formula (XVIII) shown above.

In one embodiment, the pharmaceutical formulation for a controlled release dosage form of at least one compound having Formula (I), Formula (II) or Formula (III) may further comprise a composition of a coating layer coated on the controlled release layer. The purpose of the coating layer is to prevent the controlled release layer from being damaged or eroded and lose its ability to control release.

The composition of the coating layer may comprise hydroxypropyl methyl cellulose, polyethylene glycol, lactose, Talc, titanium dioxide, etc., or a combination thereof. Alternatively, the composition of the coating layer also can be a commercial composition, such as Opadry film coating or Kollicoat film coating, but it is not limited thereto.

In the embodiment in which the pharmaceutical formulation for a controlled release dosage form of at least one compound having Formula (I), Formula (II) or Formula (III) of the present disclosure further comprise a composition of a coating layer coated on the controlled release layer, the composition of a particle carrier may occupy about 35-98% by weight, the composition of a drug layer may occupy about 1-64% by weight, the composition of a controlled release layer may occupy about 1-50% by weight, and the composition of a coating layer may occupy about 1-35% by weight, wherein the at least one compound having Formula (I), Formula (II) or Formula (III), or its geometric isomer, enantiomer, diastereomer or pharmaceutically acceptable salt may occupy about 1-99% by weight of the composition of a drug layer.

Any foregoing pharmaceutical formulation for a controlled release dosage form of at least one compound having Formula (I), Formula (II) or Formula (III) is capable of decreasing a dosage and/or dosing frequency to a subject in need of being administered at least one compound having Formula (I), Formula (II) or Formula (III), or its geometric isomer, enantiomer, diastereomer or pharmaceutically acceptable salt.

Moreover, the subject in need of being administered at least one compound having Formula (I), Formula (II) or Formula (III), or its geometric isomer, enantiomer, diastereomer or pharmaceutically acceptable salt may comprise a subject suffering from a disease which can be treated by at least one compound having Formula (I), Formula (II) or Formula (III), or its geometric isomer, enantiomer, diastereomer or pharmaceutically acceptable salt, but it is not limited thereto. In one embodiment, the disease may comprise, but is not limited to, an autoimmune neurological disease and/or a neurodegenerative disease. In one specific embodiment, the disease may be multiple sclerosis.

The foregoing subject may include, but is not limited to, a vertebrate. The vertebrate mentioned above may include a fish, an amphibian, a reptile, a bird, or a mammal, but it is not limited thereto. Examples of mammals include, but are not limited to, a human, an orangutan, a monkey, a horse, a donkey, a dog, a cat, a rabbit, a guinea pig, a rat, and a mouse. In one embodiment, the subject is a human.

EXAMPLES

Example 1

Effects of Sobrerol and Derivatives thereof on inhibition of LPS-induced Inflammation in BV-2 Cells 1. Method BV-2 cells ($8 \times 10^3$ cells/mL) were seeded in a 96-well plate cultured under 37° C., 5% $CO_2$ overnight. The cells were divided into a naïve group (without any treatment), a control group (only treated with LPS) and experimental groups (treated with LPS and a testing compound).

The supernatant in the well was removed. After that, different concentrations of a testing compound was added to the cells to react with the cells for 1 hour (culture medium was added to the cells for a control group), and then LPS (100 ng/mL) was added to the cell.

After reacting for 24 hours, the supernatant in the plate was taken and IL-6 expressing amount was detected by Mouse IL-6 ELISA Ready-SET-Go (Invitrogen; Cat. No. 88-7064-88) according to the manufacturer's recommended procedure.

Moreover, 50 μl of culturing medium containing MTT (0.5 mg/mL) was added to the cell part in the plate and cultured under 37° C. and 5% $CO_2$ for 90 minutes, and then 150 μL DMSO was added to the plate and the plate was shaken for 5-10 minutes. Finally, $OD_{570}$ was read by a continuous wavelength microplate analyzer, and cell viability was calculated using the following formula:

Cell viability (%)=(OD value of the experimental group/OD value of the control group)×100.

$CC_{50}$ value for cell viability of a testing compound and $IC_{50}$ value for IL-6 expression of a testing compound were calculated based on cell viabilities at different concentrations of the testing compound and IL-6 expression amounts of the cells at different concentrations of the testing compound, respectively.

2. Results
The results are shown in Table 1.

TABLE 1

CC$_{50}$ values for cell viability and IC$_{50}$ values for IL-6 expression of sobrerol and derivatives thereof

| Compound Number | Formula | Molecular weight | IC$_{50}$ for IL-6 expression (μM) | CC$_{50}$ for cell viability (μM) |
| --- | --- | --- | --- | --- |
| SK2 ((−) trans-sobrerol) | (structure shown) | 170.25 | 182.8 ± 21.8 | >200 |
| TMUS-0124-4a | Formula (V) | 274.36 | 62.2 | >100 |
| TMUS-0124-4b | Formula (VI) | 288.39 | 32.1 | >100 |
| TMUS-0124-4c | Formula (VII) | 302.41 | 38.2 | >100 |
| TMUS-0124-4d | Formula (VIII) | 319.36 | 48.1 | >100 |
| TMUS-0124-4e | Formula (IX) | 304.39 | 50.8 | >100 |
| TMUS-0124-4f | Formula (X) | 268.4 | 38.0 | >100 |
| TMUS-0503-m1 | Formula (XI) | 184.28 | <10 | >100 |
| TMUS-0503-b1 | Formula (XII) | 260.38 | <10 | >100 |
| TMUS-0503-o1 | Formula (XIII) | 168.24 | <10 | >100 |

TABLE 1-continued

CC$_{50}$ values for cell viability and IC$_{50}$ values for IL-6 expression of sobrerol and derivatives thereof

| Compound Number | Formula | Molecular weight | IC$_{50}$ for IL-6 expression (μM) | CC$_{50}$ for cell viability (μM) |
|---|---|---|---|---|
| TMUS-0503-c1 | Formula (XVII) | 152.24 | 30-100 | >100 |
| TMUS-0503-c2 | Formula (XVIII) | 249.15 | 30-100 | >100 |
| TMUS-0503-H2 | Formula (XIV) | 113.98 | <10 | >100 |
| TMUS-0503-H3 | Formula (XV) | 172.27 | 30-100 | >100 |
| TMUS-0503-H4 | Formula (XVI) | 172.27 | 30-100 | >100 |

Based on the results shown in above Table 1, it is clear that the derivatives of sobrerol which are tested are capable of inhibiting LPS-induced IL-6 expression in BV-2 cells. In other words, the derivatives of sobrerol which are tested can inhibit LPS-induced inflammation.

Example 2

Preparation of Liquid Dosage Form of Sobrerol 30 mg powder of (−) trans-sobrerol, 60 mg PEO-PPO-PEO (poly(ethylene oxide)$_{76}$-poly(propylene oxide)$_{30}$-poly(ethylene oxide)$_{76}$; MW 6800) (6%) and 400 mg powder of 2-hydroxypropyl-beta cyclodextrin (40%) were dissolved in 1 ml deionized water (%: mg/100 μl water) in a microcentrifuge tube to form a mixture. After that, the microcentrifuge tube was shaken under room temperature until the mixture therein become transparent to complete the preparation of a liquid dosage form of sobrerol.

Example 3

A. Controlled Release Dosage Form of 17% (−)Trans-Sobrerol

1. Preparation of Controlled Release Dosage Form of 17% Trans-Sobrerol 50 g of (−)trans-sobrerol and 20 g of polyvinylpyrrolidone were dissolved in 250 g of ethanol to form a first spraying solution. 200 g of microcrystalline cellulose spheres (particle size was about 25-35 mesh number, about 500-710 μm) was introduced into a fluid-bed granulator and spraying-coated with the spraying solution (spray volume: 0.6-2.0 g/minute; spray air pressure: 0.4-0.6 kg/cm$^2$; exhaust air temperature: 20-30° C.; inlet air temperature: 25-40° C.) to obtain (−)trans-sobrerol drug carrying-particles (uncoated-drug carrying particles).

18.6 g of ethyl cellulose and 2.1 g of hydroxypropyl methyl cellulose were dissolved in a mixture solution of 185.6 g of ethanol and 20.7 g of pure water (with a weight ratio of about 9:1) and stirred to be evenly dispersed in the mixture solution to form a second spraying solution.

270 g of (−)trans-sobrerol drug carrying-particles was introduced into a fluid-bed granulator and spraying-coated with the second spraying solution (spray volume: 0.2-1.0 g/minute; spray air pressure: 0.4-0.6 kg/cm², exhaust air temperature: 20-26° C.; inlet air temperature: 23-30° C.) to obtain controlled release particles with 17% trans-sobrerol (coated-drug carrying particles).

2. Dissolution Testing for Controlled Release Particles with 17% Trans-Sobrerol

Dissolution testing was performed on the uncoated-drug carrying particles (without controlled release effect) and coated-drug carrying particles (with controlled release effect) obtained above to compare the dissolution rates of the two kinds of particles.

Basket method was used in the dissolution testing, and the process of the dissolution testing is described in the following.

1000 ml pure water was added to a testing container, and then the testing container was configured to a dissolution tester, and the water temperature was set to 37° C. A testing sample (191 mg uncoated-drug carrying particles or 200 mg coated-drug carrying particles) was placed in a basket. When the temperature of the water in the testing container reached to 37.0±0.5° C., the basket was descended to the testing container with a stirring rate of 75 rpm to begin the dissolution (initial point). Samplings were performed at 5, 15, 30, 60, 120, 180 and 240 minutes after the initial point, respectively, and sampling volume was 10 ml. The samples were filtered by a 0.45 μm filter and then component contents thereof were analyzed by high performance liquid chromatography (HPLC), respectively.

The results of the dissolution testing for controlled release particles with 17% trans-sobrerol (coated-drug carrying particles) and trans-sobrerol drug carrying-particles (uncoated-drug carrying particles) are shown in FIG. 1.

The results show that 15 minutes after the beginning of the dissolution testing in which pure water was used as the solvent, the dissolution rate of the trans-sobrerol drug carrying-particles (uncoated-drug carrying particles) was 100% while the dissolution rate of the controlled release particles with 17% trans-sobrerol (coated-drug carrying particles) was less than 20%. 120 minutes after the beginning of the dissolution testing, the dissolution rate of the controlled release particles with 17% trans-sobrerol (coated-drug carrying particles) was about 80%. According to the results mentioned above, it is confirmed that the controlled release layer has controlled release effect on the dissolution rate of trans-sobrerol.

B. Controlled Release Dosage Form of 20% (+)(−)Trans-Sobrerol

1. Preparation of Controlled Release Dosage Form of 20% (+)(−)Trans-Sobrerol 60 g of (+)(−)trans-sobrerol and 24 g of polyvinylpyrrolidone were dissolved in 300 g of ethanol to form a first spraying solution. 200 g of microcrystalline cellulose spheres (particle size was about 25-35 mesh number, about 500-710 μm) was introduced into a fluid-bed granulator and spraying-coated with the spraying solution (spray volume: 0.6-2.0 g/minute; spray air pressure: 0.4-0.6 kg/cm²; exhaust air temperature: 20-30° C.; inlet air temperature: 25-40° C.) to obtain (+)(−)trans-sobrerol drug carrying-particles (uncoated-drug carrying particles).

20.3 g of ethyl cellulose and 2.3 g of hydroxypropyl methyl cellulose were dissolved in a mixture solution of 202.5 g of ethanol and 22.5 g of pure water (with a weight ratio of about 9:1) and stirred to be evenly dispersed in the mixture solution to form a second spraying solution.

284 g of (+)(−)trans-sobrerol drug carrying-particles was introduced into a fluid-bed granulator and spraying-coated with the second spraying solution (spray volume: 0.2-1.0 g/minute; spray air pressure: 0.4-0.6 kg/cm²; exhaust air temperature: 20-35° C.; inlet air temperature: 25-40° C.) to obtain controlled release particles with 20% (+)(−)trans-sobrerol (coated-drug carrying particles). The controlled release particles with 20% (+)(−)trans-sobrerol (coated-drug carrying particles) were made in two batches.

2. Dissolution Testing for Controlled Release Particles with 20% Sobrerol

Dissolution testing was performed on the uncoated-drug carrying particles (without controlled release effect) and coated-drug carrying particles (with controlled release effect) obtained above to compare the dissolution rates of the two kinds of particles.

Basket method was used in the dissolution testing, and the process of the dissolution testing is described in the following.

1000 ml pure water was added to a testing container, and then the testing container was configured to a dissolution tester, and the water temperature was set to 37° C. A testing sample (193 mg uncoated-drug carrying particles or 208 mg coated-drug carrying particles) was placed in a basket. When the temperature of the water in the testing container reached to 37.0±0.5° C., the basket was descended to the testing container with a stirring rate of 75 rpm to begin the dissolution (initial point). Samplings were performed at 5, 15, 30, 60, 120, 180 and 240 minutes after the initial point, respectively, and sampling volume was 10 ml. The samples were filtered by a 0.45 μm filter and then component contents thereof were analyzed by high performance liquid chromatography (HPLC), respectively.

Figure 2:
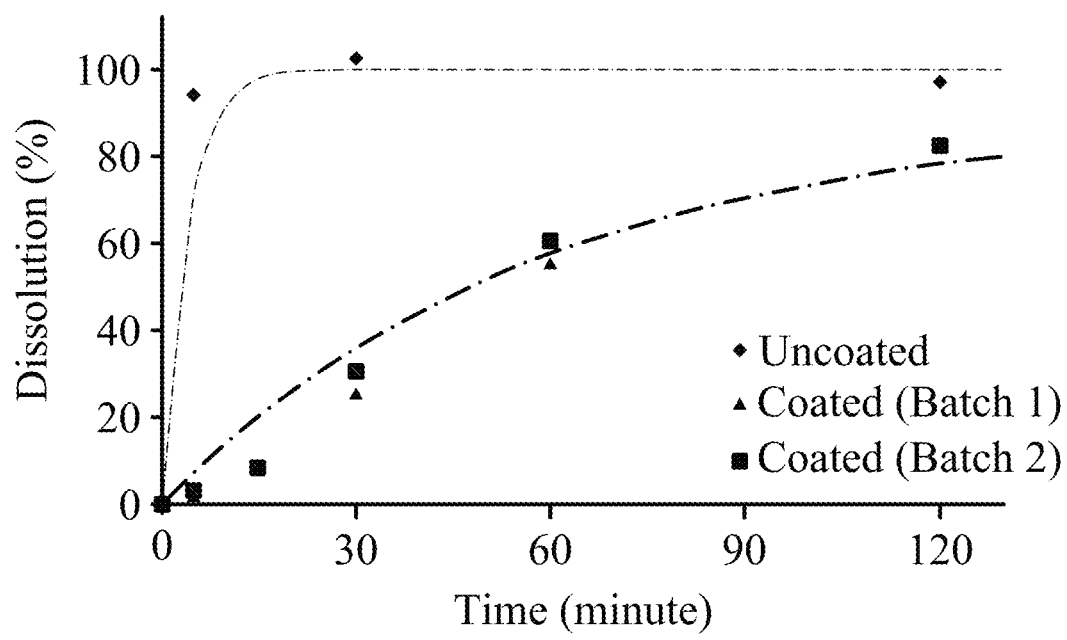
FIG. 2 shows the results of the dissolution testing for controlled release particles with 20% (+)(−)trans-sobrerol (coated-drug carrying particles) and (+)(−)trans-sobrerol drug carrying-particles (uncoated-drug carrying particles)

The results of the dissolution testing for controlled release particles with 20% sobrerol (coated-drug carrying particles) and sobrerol drug carrying-particles (uncoated-drug carrying particles) are shown in FIG. 2.

The results show that 30 minutes after the beginning of the dissolution testing in which pure water was used as the solvent, the dissolution rate of the sobrerol drug carrying-particles (uncoated-drug carrying particles) was 100% while the dissolution rates of the two batches of controlled release particles with 20% sobrerol (coated-drug carrying particles) both were less than 40%. 120 minutes after the beginning of the dissolution testing, the dissolution rates of the two batches of controlled release particles with 20% sobrerol (coated-drug carrying particles) both were about 80%. According to the results mentioned above, it is confirmed that the controlled release layer has controlled release effect on the dissolution rate of sobrerol.

C. Controlled Release Dosage Form of 8% (+)(−)Trans-Sobrerol

1. Preparation of Controlled Release Dosage Form of 8% (+)(−)Trans-Sobrerol 20 g of (+)(−)trans-sobrerol and 8 g of polyvinylpyrrolidone were dissolved in 100 g of ethanol to form a first spraying solution. 200 g of microcrystalline cellulose spheres (particle size was about 25-35 mesh number, about 500-710 μm) was introduced into a fluid-bed granulator and spraying-coated with the spraying solution (spray volume: 0.6-1.4 g/minute; spray air pressure: 0.4-0.6 kg/cm²; exhaust air temperature: 20-26° C.; inlet air temperature: 22-32° C.) to obtain (+)(−)trans-sobrerol drug carrying-particles (uncoated-drug carrying particles).

18.56 g of ethyl cellulose and 2.07 g of hydroxypropyl methyl cellulose were dissolved in a mixture solution of 185.6 g of ethanol and 20.7 g of pure water (with a weight ratio of about 9:1) and stirred to be evenly dispersed in the mixture solution to form a second spraying solution.

228 g of (+)(−)trans-sobrerol drug carrying-particles was introduced into a fluid-bed granulator and spraying-coated with the second spraying solution (spray volume: 0.4-1.2 g/minute; spray air pressure: 0.4-0.6 kg/cm², exhaust air temperature: 20-26° C.; inlet air temperature: 23-30° C.) to obtain controlled release particles with 8% (+)(−)trans-sobrerol (coated-drug carrying particles).

2. Dissolution testing for controlled release particles with 8% sobrerol

Dissolution testing was performed on the uncoated-drug carrying particles (without controlled release effect) and coated-drug carrying particles (with controlled release effect) obtained above to compare the dissolution rates of the two kinds of particles.

Basket method was used in the dissolution testing, and the process of the dissolution testing is described in the following.

1000 ml pure water was added to a testing container, and then the testing container was configured to a dissolution tester, and the water temperature was set to 37° C. A testing sample (190 mg uncoated-drug carrying particles or 204 mg coated-drug carrying particles) was placed in a basket. When the temperature of the water in the testing container reached to 37.0±0.5° C., the basket was descended to the testing container with a stirring rate of 75 rpm to begin the dissolution (initial point). Samplings were performed at 5, 15, 30, 60, 120, 180 and 240 minutes after the initial point, respectively, and sampling volume was 10 ml. The samples were filtered by a 0.45 μm filter and then component contents thereof were analyzed by high performance liquid chromatography (HPLC), respectively.

Figure 3:
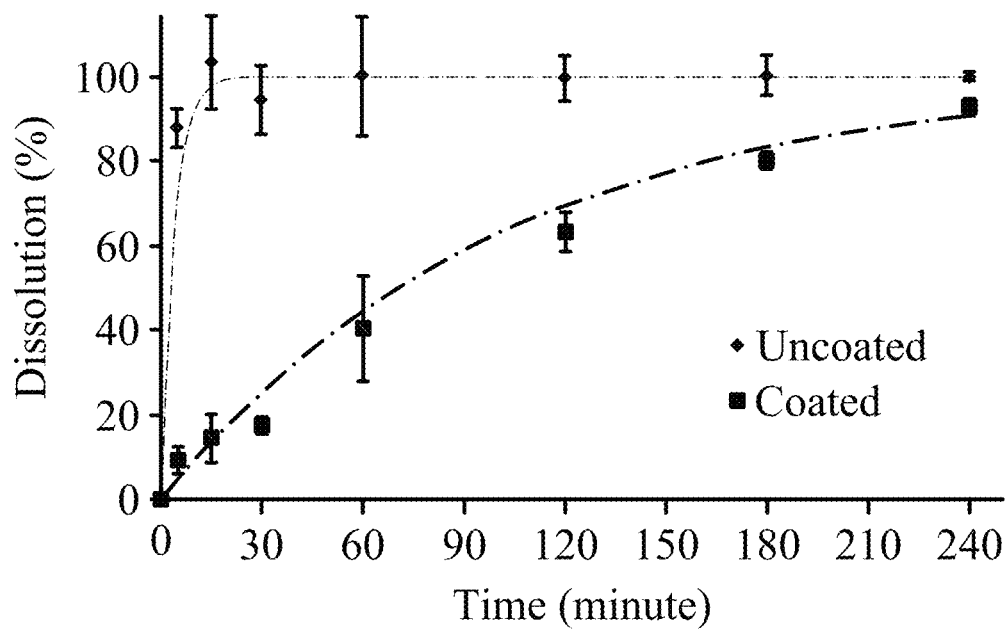
FIG. 3 shows the results of the dissolution testing for controlled release particles with 8% (+)(−)trans-sobrerol (coated-drug carrying particles) and (+)(−)trans-sobrerol drug carrying-particles (uncoated-drug carrying particles)

The results of the dissolution testing for controlled release particles with 8% sobrerol (coated-drug carrying particles) and sobrerol drug carrying-particles (uncoated-drug carrying particles) are shown in FIG. 3.

The results show that 15 minutes after the beginning of the dissolution testing in which pure water was used as the solvent, the dissolution rate of the sobrerol drug carrying-particles (uncoated-drug carrying particles) was 100% while the dissolution rate of the controlled release particles with 8% sobrerol (coated-drug carrying particles) was less than 20%. 180 minutes after the beginning of the dissolution testing, the dissolution rate of the controlled release particles with 8% sobrerol (coated-drug carrying particles) was about 80%. According to the results mentioned above, it is confirmed that the controlled release layer has controlled release effect on the dissolution rate of sobrerol.

D. Controlled Release Dosage Form of 32% (+)(−)Trans-Sobrerol

1. Preparation of Controlled Release Dosage Form of 32% (+)(−)Trans-Sobrerol 125 g of (+)(−)trans-sobrerol and 50 g of polyvinylpyrrolidone were dissolved in 625 g of ethanol to form a first spraying solution. 200 g of microcrystalline cellulose spheres (particle size was about 25-35 mesh number, about 500-710 μm) was introduced into a fluid-bed granulator and spraying-coated with the spraying solution (spray volume: 0.6-2.8 g/minute; spray air pressure: 0.4-0.75 kg/cm²; exhaust air temperature: 20-26° C.; inlet air temperature: 24-31° C.) to obtain (+)(−)trans-sobrerol drug carrying-particles (uncoated-drug carrying particles).

18.56 g of ethyl cellulose and 2.07 g of hydroxypropyl methyl cellulose were dissolved in a mixture solution of 185.6 g of ethanol and 20.7 g of pure water (with a weight ratio of about 9:1) and stirred to be evenly dispersed in the mixture solution to form a second spraying solution.

375 g of (+)(−)trans-sobrerol drug carrying-particles was introduced into a fluid-bed granulator and spraying-coated with the second spraying solution (spray volume: 0.8-1.2 g/minute; spray air pressure: 0.8-0.9 kg/cm²; exhaust air temperature: 20-24° C.; inlet air temperature: 22-29° C.) to obtain controlled release particles with 32% (+)(−)trans-sobrerol (coated-drug carrying particles).

2. Dissolution Testing for Controlled Release Particles with 32% Sobrerol

Dissolution testing was performed on the uncoated-drug carrying particles (without controlled release effect) and coated-drug carrying particles (with controlled release effect) obtained above to compare the dissolution rates of the two kinds of particles.

Basket method was used in the dissolution testing, and the process of the dissolution testing is described in the following.

1000 ml pure water was added to a testing container, and then the testing container was configured to a dissolution tester, and the water temperature was set to 37° C. A testing sample (190 mg uncoated-drug carrying particles or 198 mg coated-drug carrying particles) was placed in a basket. When the temperature of the water in the testing container reached to 37.0±0.5° C., the basket was descended to the testing container with a stirring rate of 75 rpm to begin the dissolution (initial point). Samplings were performed at 5, 15, 30, 60, 120, 180 and 240 minutes after the initial point, respectively, and sampling volume was 10 ml. The samples were filtered by a 0.45 μm filter and then component contents thereof were analyzed by high performance liquid chromatography (HPLC), respectively.

Figure 4:
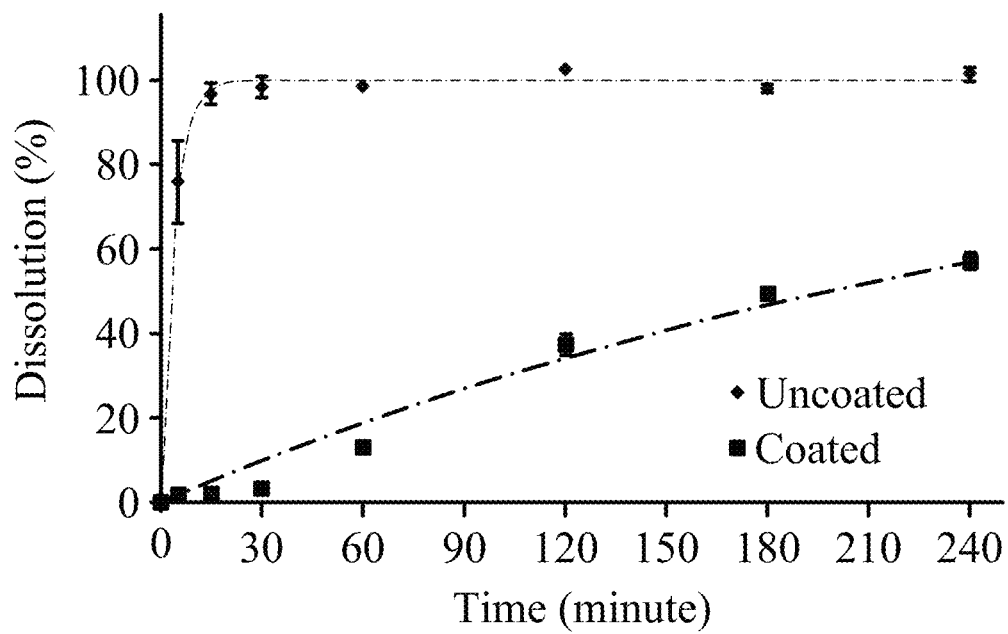
FIG. 4 shows the results of the dissolution testing for controlled release particles with 32% (+)(−)trans-sobrerol (coated-drug carrying particles) and (+)(−)trans-sobrerol drug carrying-particles (uncoated-drug carrying particles) (uncoated-drug carrying particles)

The results of the dissolution testing for controlled release particles with 32% sobrerol (coated-drug carrying particles) and sobrerol drug carrying-particles (uncoated-drug carrying particles) are shown in FIG. 4.

The results show that 15 minutes after the beginning of the dissolution testing in which pure water was used as the solvent, the dissolution rate of the sobrerol drug carrying-particles (uncoated-drug carrying particles) was 100% while the dissolution rate of the controlled release particles with 32% sobrerol (coated-drug carrying particles) was less than 5%. 240 minutes after the beginning of the dissolution testing, the dissolution rate of the controlled release particles with 32% sobrerol (coated-drug carrying particles) was about 57%. According to the results mentioned above, it is confirmed that the controlled release layer has controlled release effect on the dissolution rate of sobrerol.

Example 4

MOG Induced IFN-γ Secretion and IL-2 Secretion in Splenocyte Isolated from Mice of Experimental Autoimmune Encephalomyelitis (EAE) Model EAE was induced in C57BL/6 mice. The mice were immunized on Day 0 by subcutaneous injection with 200 μg of myelin oligodendrocyte glycoprotein (MOG) in incomplete Freund's adjuvant (IFA) containing 400 μg of heat-killed Mycobaterium tuberculosis H37Ra. Pertussis toxin (500 ng) was intraperitoneally injected on Day 0 and Day 2 after the mice were immunized with the emulsion. The mice were sacrifice on Day 30 post-immunization. Spleens of the mice were harvest and then splenocytes were isolated and cultured in presence or absence of the 20 μg/ml MOG peptide in 10% FBS RPMI1640 medium. Testing compound was added to the culture and maintained at 37° C. 5% CO₂ for 48 hours. The concentrations of IFN-γ and IL-2 in the supernatant of the culture were determined by ELISA according to the manufacturer's instructions.

2. Results

The results are shown in Table 2.

TABLE 2

IFN-γ inhibition and IL-2 inhibition of sobrerol and derivatives thereof

| Compound Number | Formula | Molecular weight | Concentration μM | IFN-γ inhibition % | IL-2 inhibition % |
|---|---|---|---|---|---|
| SK0 ((+)(−) trans-Sobrerol) | 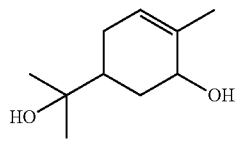<br>Formula (IV) | 170.25 | 300 | 10 | 16 |
| SK1 ((+) trans-Sobrerol) | 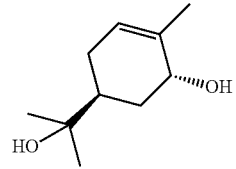 | 170.25 | 200 | 24 | 0 |
| SK2 ((−) trans-sobrerol) | 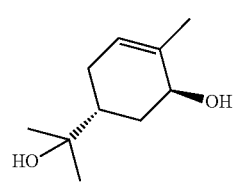 | 170.25 | 200 | 34 | 0 |
| TMUS-0124-4a | Formula (V) | 274.36 | 200 | 77 | 31 |
| TMUS-0124-4b | Formula (VI) | 288.39 | 100 | 88 | 48 |
| TMUS-0124-4c | 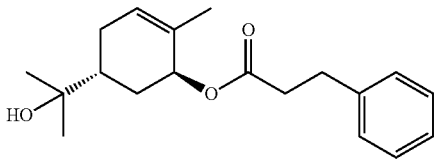<br>Formula (VII) | 302.41 | 200 | 78 | 23 |
| TMUS-0124-4d | 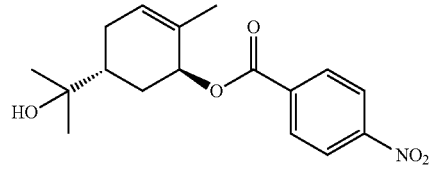<br>Formula (VIII) | 319.36 | 200 | 79 | 22 |
| TMUS-0124-4e | 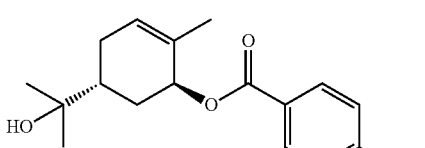<br>Formula (IX) | 304.39 | 100 | 86 | 59 |

TABLE 2-continued

IFN-γ inhibition and IL-2 inhibition of sobrerol and derivatives thereof

| Compound Number | Formula | Molecular weight | Concentration μM | IFN-γ inhibition % | IL-2 inhibition % |
|---|---|---|---|---|---|
| TMUS-0124-4f | Formula (X) | 268.4 | 200 | 59 | 8 |
| TMUS-0503-m1 | Formula (XI) | 184.28 | 100 | 17 | 21 |
| TMUS-0503-b1 | Formula (XII) | 260.38 | 300 | 20 | 15 |
| TMUS-0503-o1 | Formula (XIII) | 168.24 | 200 | 56 | 40 |
| TMUS-0503-c1 | Formula (XVII) | 152.24 | 300 | 23 | 22 |
| TMUS-0503-c2 | Formula (XVIII) | 249.15 | 100 | 31 | 13 |
| TMUS-0503-H2 | Formula (XIV) | 113.98 | 100 | 33 | 16 |
| TMUS-0503-H4 | Formula (XVI) | 172.27 | 300 | 42 | 19 |

Example 5

Animal Experiment

A. Material a. Animals

The female C57BL/6 mice, aged 8 weeks old, purchased from the National Laboratory Animal Center (NLAC, Taiwan) were used in this study. The animals of C57BL/6 mice had been widely used with abundant references and data, and fit to the evaluation of the Experimental autoimmune encephalomyelitis (EAE) model. The mice were housed with free access to water and food under a constant environment that maintained at 23±2° C., relative humidity 40-70% and on a 12:12-hour light-dark cycle at the animal research facility of the Industrial Technology Research Institute (ITRI, Taiwan).

In order to ensure the health of the animals, clinical observation and record were performed by veterinarians and investigators of ITRI during the period of quarantine and experiment daily, respectively. The animal use protocol listed below has been reviewed and approved by the Institutional Animal Care and Use Committee (IACUC) of ITRI.

b. Reagents

Incomplete Freund's adjuvant (IFA) (Sigma-Aldrich, USA); Myelin Oligodendrocyte glycoprotein ($MOG_{35-55}$) peptide (Kelowna International Scientific company, Taiwan); Pertussis Toxin (List Biological Laboratories, USA); *Mycobacterium tuberculosis* H37RA (Difco Laboratories, Germany); A mixture of (+) trans-sobrerol and (−) trans-sobrerol (Mucoflux capsules); (−) trans-sobrerol (Sigma-Aldrich)

B. Methods

3. Therapeutic Administration Experiment 3-1 Testing Drug Administration after Experimental Autoimmune Encephalomyelitis (EAE) Induction and Clinical Assessment For induction of EAE, female C57BL/6 mice were subcutaneously injected with 200 µl emulsion including 200 µg $MOG_{35-55}$ peptide and 400 µg *Mycobacterium tuberculosis* H37Ra, then intraperitoneally injected with 500 ng pertussis toxin, and after 48 hours, the mice were subjected another intraperitoneal injection with 500 ng pertussis toxin.

From Day 7 post to the induction, the EAE clinical symptoms of the mice were recorded daily according to the recognized Ataxia score (grading of nervous system disorder) and EAE score as the scoring criteria (description of Ataxia score and EAE score are as follows). When the mice began to appear Ataxia score 0++, the mice were grouped by S-type grouping method and administration of testing drug (a mixture of (+) trans-sobrerol and (−) trans-sobrerol (Mucoflux capsules), (−) trans-sobrerol (Sigma-Aldrich) or a liquid dosage form of (−) trans-sobrerol prepared in Example 2 mentioned above) was begun and continued for 14 days. On Day 15 of the administration of testing drug, the mice were sacrificed, and blood or related organs thereof were collected for subsequent analysis.

The criteria of Ataxia score that modified from Metten et al (2004) are shown as follows: 0+: The rear foot of the animal is splayed while moving, swing left and right, and gait imbalance; 0++: When grasping the rear neck of the animal to observe whether its tail can be raised by itself and to test the tensile strength of its tail by fingers, the tail appears unable to be raised by itself as well as reduced tension.

The criteria of EAE score are shown as follows: Score 0: no EAE symptoms; Score 0.5: Temporal weak tail, sometimes raised; Score 1: Limp tail, unable to lift normally; Score 2: Paralyzed tail or slightly hind limb weakness; Score 3: Moderate to severe hind limb paralysis or mild forelimb weakness; Score 4: Complete hind limb paralysis or moderate to severe forelimb weakness; Score 5: Limb paralysis accompanied by incontinence or presenting a dying state; Score 6: Death.

3-2. Histology and Immunohistochemistry

The mice were euthanized at day 15 post to onset of EAE. Spinal cord was removed and fixed in 10% phosphate-buffered formaldehyde. Paraffin-embedded 3 µm-thick cross sections of spinal cord were stained with hematoxylin and eosin in order to confirm tissue lesion. Another slides were stained with Luxol fast blue for examination of demyelination. Lesions were evaluated based on demyelination, inflammation, axonal swelling and gliosis which are scored based on the criteria shown in Table 2:

TABLE 2

| Lesion | Score | Description |
|---|---|---|
| Demyelination | 0 | No demyelination |
|  | 1 | Few, scattered demyelination |
|  | 2 | Small groups of demyelination |
|  | 3 | Large groups of demyelination |
|  | 4 | Massive demyelination over one half of the white matter |
|  | 5 | Widespread demyelination |
| Inflammatory | 0 | No inflammatory cells |
|  | 1 | Few, scattered inflammatory cells |
|  | 2 | Inflammatory cells infiltrate into perivascular cuffs |
|  | 3 | Perivascular cuffing with extension into parenchyma |
|  | 4 | Extensive perivascular cuffing with increasing subarachnoid and parenchymal inflammation |
| Axonal swelling | 0 | No axonal swelling |
|  | 1 | Few, scattered swollen axons |
|  | 2 | Small groups of swollen axons |
|  | 3 | Large groups of swollen axons |
| Gliosis | 0 | No gliosis |
|  | 1 | Minimal (1-10%) |
|  | 2 | Slight (11-25%) |
|  | 3 | Moderate (26-50%) |
|  | 4 | Moderately severe (51-75%) |
|  | 5 | Severe/high (76-100%) |

4. Prophylaxis Administration Experiment

Testing Drug Administration after Experimental Autoimmune Encephalomyelitis (EAE) Induction and Before Experimental Autoimmune Encephalomyelitis (EAE) Signs Onset and Clinical Assessment For induction of EAE, female C57BL/6 mice were subcutaneously injected with 200 µl emulsion including 200 µg $MOG_{35-55}$ peptide and 400 µg *Mycobacterium tuberculosis* H37Ra, then intraperitoneal injected with 500 ng pertussis toxin, and after 48 hours, the mice were subjected another intraperitoneal injection with 500 ng pertussis toxin.

From Day 7 post to the induction, the mice were grouped according the weight by S-type grouping method and administration of testing drug ((−) trans-sobrerol (Sigma-Aldrich) was begun and continued for 14 days. On Day 21 after $MOG_{35-55}$ immunization, the mice were sacrificed, and blood or related organs thereof were collected for subsequent analysis. The EAE clinical symptoms of the mice were recorded daily according to the EAE score as the scoring criteria (description of Ataxia score and EAE score are as follows).

The criteria of EAE score are shown as follows: Score 0: no EAE symptoms; Score 0.5: Temporal weak tail, sometimes raised; Score 1: Limp tail, unable to lift normally;

Score 2: Paralyzed tail or slightly hind limb weakness; Score 3: Moderate to severe hind limb paralysis or mild forelimb weakness; Score 4: Complete hind limb paralysis or moderate to severe forelimb weakness; Score 5: Limb paralysis accompanied by incontinence or presenting a dying state; Score 6: Death.

C. Results

1. Therapeutic Administration Experiment 1-1. Administration of (−) Trans-Sobrerol after Experimental Autoimmune Encephalomyelitis (EAE) Induction (−) trans-sobrerol was dissolved in vehicle (DMSO:CrEL:saline=10:10:80) to form a solution of (−) trans-sobrerol.

Based on method described in the section "3-1 Testing drug administration after experimental autoimmune encephalomyelitis (EAE) induction and clinical assessment" of "3. Therapeutic administration" of above "B. Methods", different doses of (−) trans-sobrerol and vehicle (DMSO:CrEL:saline=10:10:80) were administered to the EAE induced mice by different dosing frequencies and then EAE scores of the mice were evaluated.

Figure 5A:
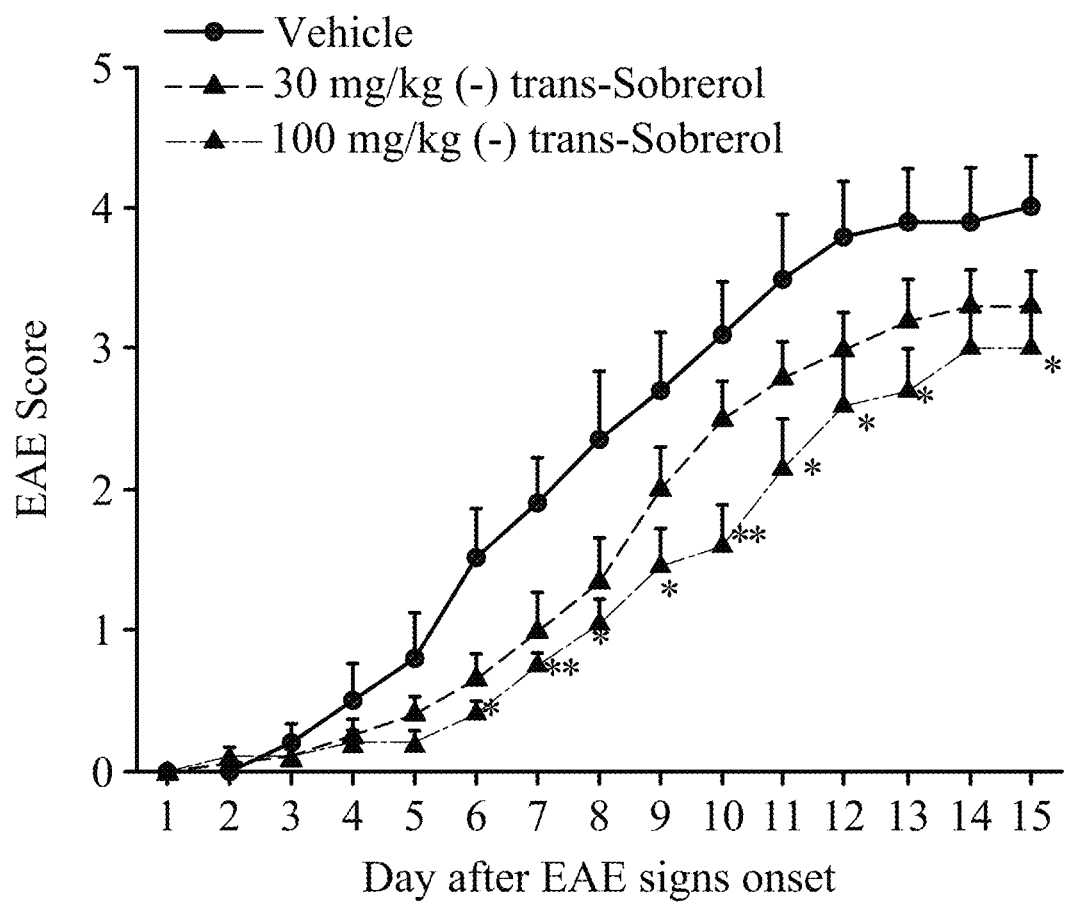
FIG. 5A shows respective EAE scores of the mice administered with 30 mg/kg and 100 mg/kg dosages of (−) trans-sobrerol and the mice administered with vehicle (DMSO:CrEL:saline=10:10:80), one time a day in a therapeutic administration experiment. Mean±standard error of the mean; n=10; *: p<0.05, **: p<0.01, as compared to the vehicle treatment group. Student's t-test.
Figure 5B:
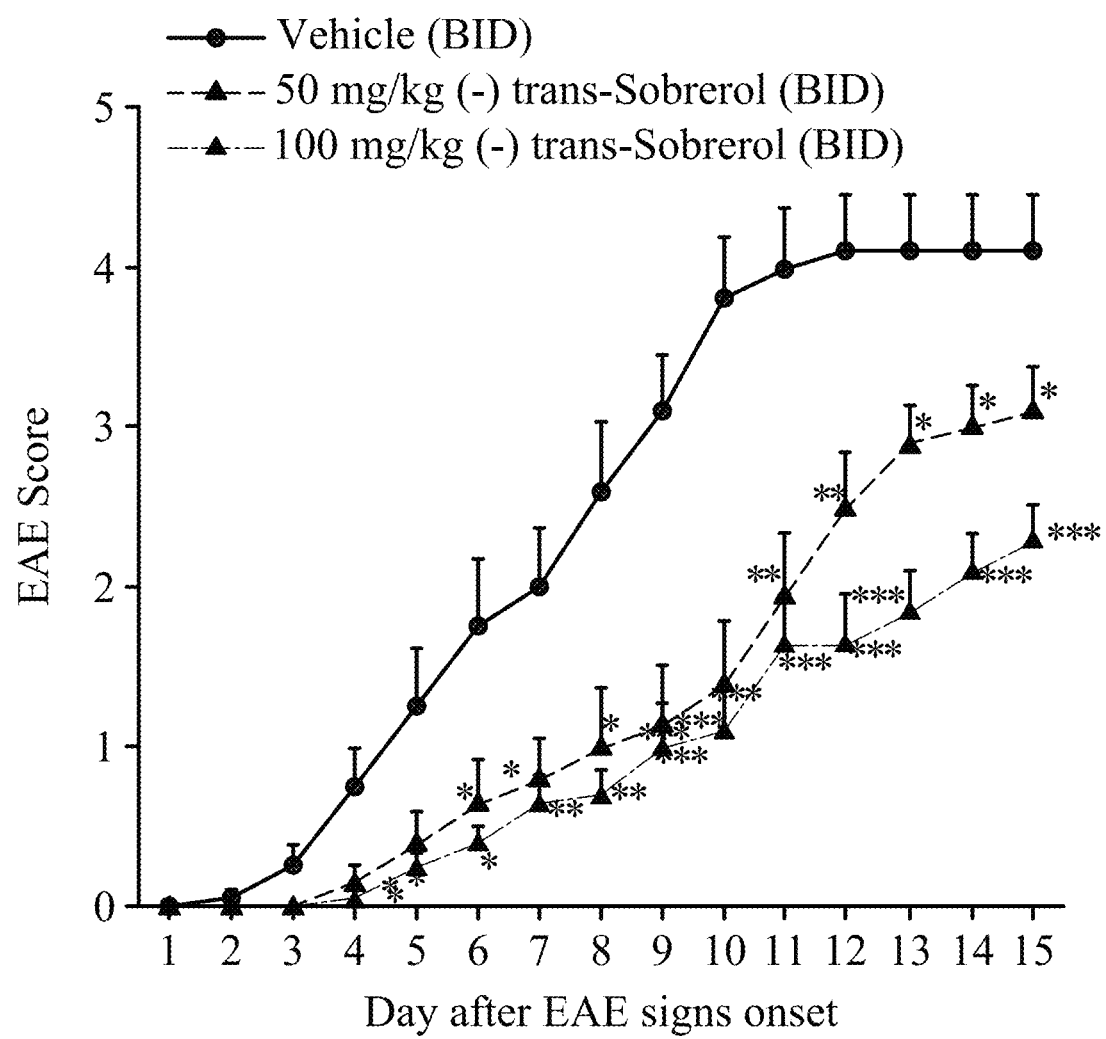
FIG. 5B shows respective EAE scores of the mice administered with 50 mg/kg and 100 mg/kg dosages of (−) trans-sobrerol, and the mice administered with vehicle (DMSO:CrEL:saline=10:10:80), two times a day in a therapeutic administration experiment. BID: two times a day (Bi in die). Mean±standard error of the mean; n=10; *: p<0.05, : p<0.01, *: p<0.001, as compared to the vehicle treatment group. Student's t-test.
Figure 5C:
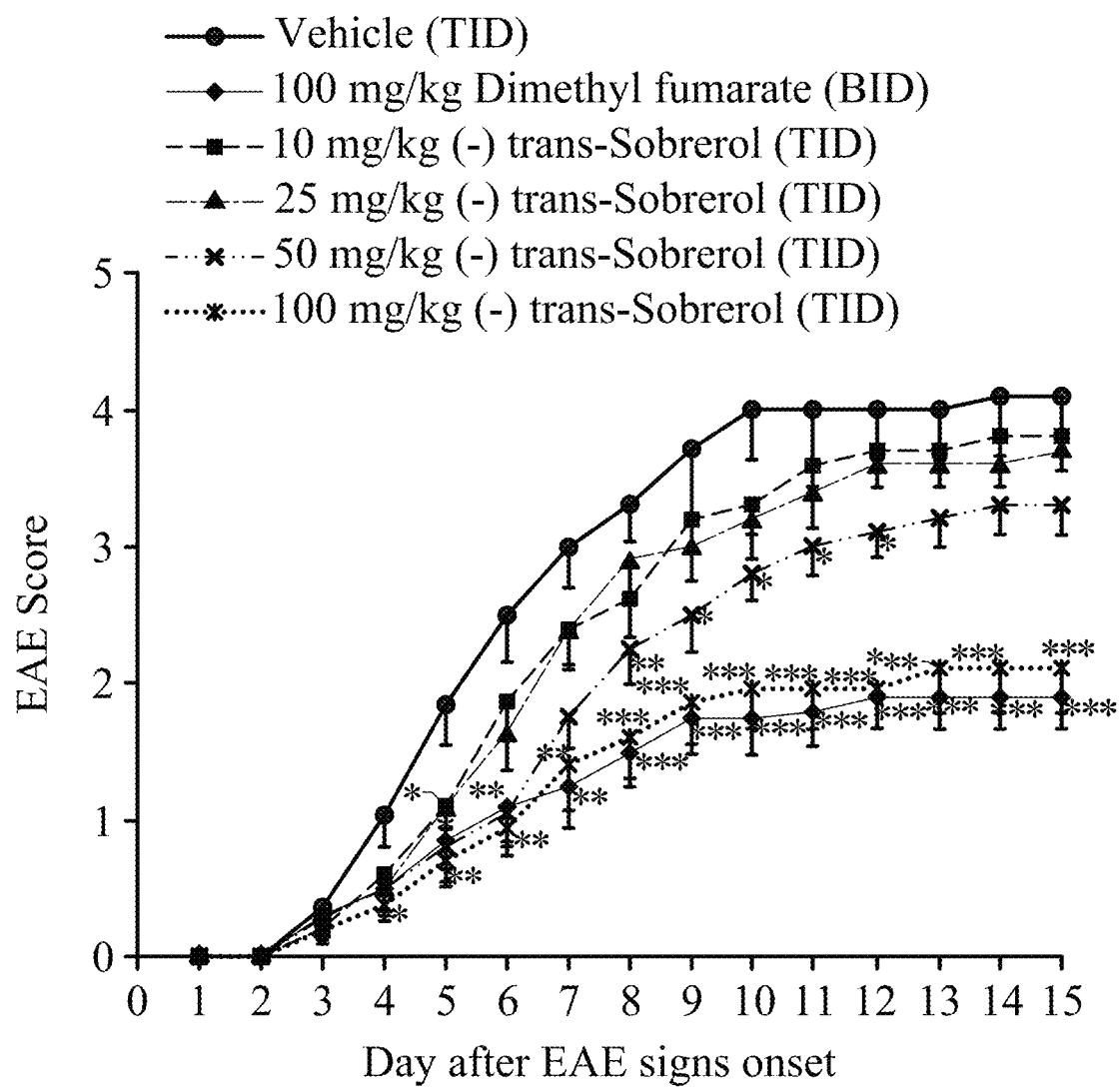
FIG. 5C shows respective EAE scores of the mice administered with 10 mg/kg, 25 mg/kg, 50 mg/kg and 100 mg/kg dosages of (−) trans-sobrerol, the mice administered with vehicle (DMSO:CrEL:saline=10:10:80), three times a day, and the mice administered with 100 mg/kg dosage of dimethyl fumarate, two times a day in a therapeutic administration experiment. BID (Bi in die): two times a day; TID (Ter in die): three times a day. Mean±standard error of the mean; n=10; *:p<0.05, :p<0.01, *: p<0.001, as compared to the vehicle treatment group. Student's t-test.

The results are shown in FIGS. 5A, 5B, and 5C. FIG. 5A shows respective EAE scores of the mice administered with 30 mg/kg and 100 mg/kg dosages of (−) trans-sobrerol and the mice administered with vehicle (DMSO:CrEL:saline=10:10:80), one time a day. FIG. 5B shows respective EAE scores of the mice administered with 50 mg/kg and 100 mg/kg dosages of (−) trans-sobrerol, and the mice administered with vehicle (DMSO:CrEL:saline=10:10:80), two times a day. FIG. 5C shows respective EAE scores of the mice administered with 10 mg/kg, 25 mg/kg, 50 mg/kg and 100 mg/kg dosages of (−) trans-sobrerol, the mice administered with vehicle (DMSO:CrEL:saline=10:10:80), three times a day, and the mice administered with 100 mg/kg dosage of dimethyl fumarate two times a day.

According to the results shown in FIGS. 5A, 5B and 5C, it is clear that (−) trans-sobrerol can significantly alleviating symptoms of EAE in the EAE induced mice.

Lesions of spinal cords of the mice were evaluated based on demyelination, inflammation, axonal swelling and gliosis based on the method described in the section "3-2. Histology and immunohistochemistry" of "3. Therapeutic administration" of above "B. Methods".

The results are shown in FIGS. 6A-6D and FIGS. 7A-7D.

Figure 6A:
FIG. 6A shows Hematoxylin and eosin stain for the spinal cords of the mice treated with 100 mg/kg dosages of (−) trans-sobrerol three times a day in a therapeutic administration experiment.
Figure 6B:
FIG. 6B shows Hematoxylin and eosin stain for the spinal cords of the mice treated with vehicle three times a day in a therapeutic administration experiment. Demyelination is indicated by the arrows.
Figure 6C:
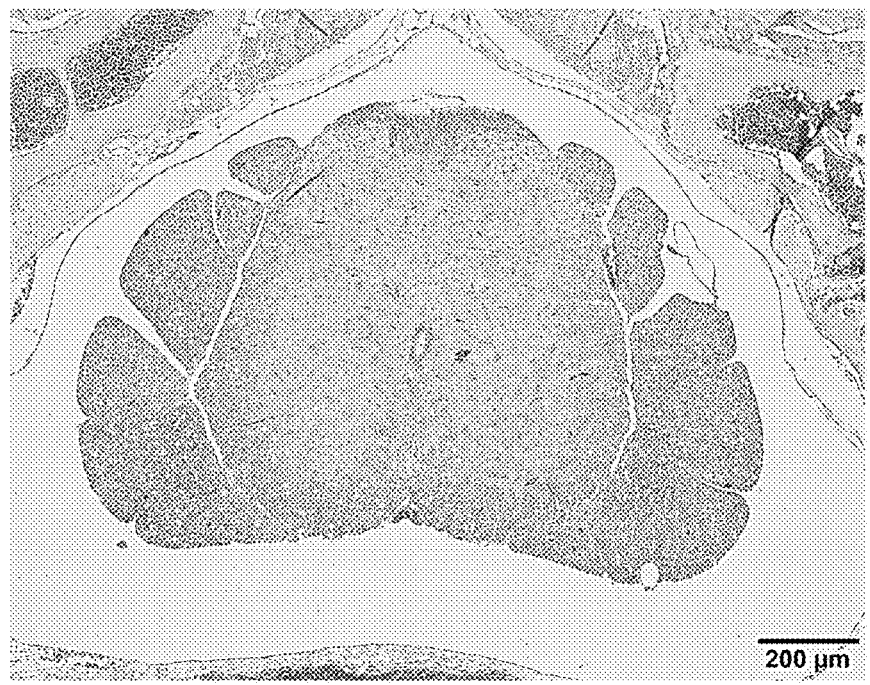
FIG. 6C shows Luxol fast blue stain for the spinal cords of the mice treated with treated with 100 mg/kg dosages of (−) trans-sobrerol three times a day in a therapeutic administration experiment.
Figure 6D:
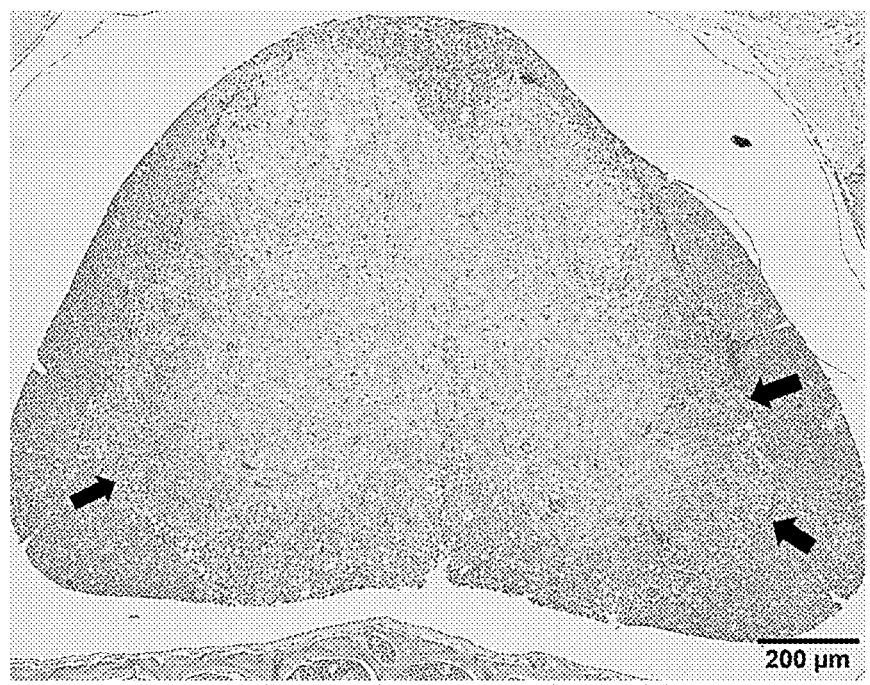
FIG. 6D shows Luxol fast blue stain for the spinal cords of the mice treated with vehicle three times a day in a therapeutic administration experiment. Demyelination is indicated by the arrows.

In FIG. 6A shows the result of hematoxylin and eosin stain for the spinal cords of the mice treated with 100 mg/kg dosages of (−) trans-sobrerol three times a day, FIG. 6B shows the results of hematoxylin and eosin stain for the spinal cords of the mice treated with vehicle three times a day, FIG. 6C shows the result of Luxol fast blue stain for the spinal cords of the mice treated with treated with 100 mg/kg dosages of (−) trans-sobrerol three times a day, and FIG. 6D shows the results of Luxol fast blue stain for the spinal cords of the mice treated with vehicle three times a day.

Figure 7A:
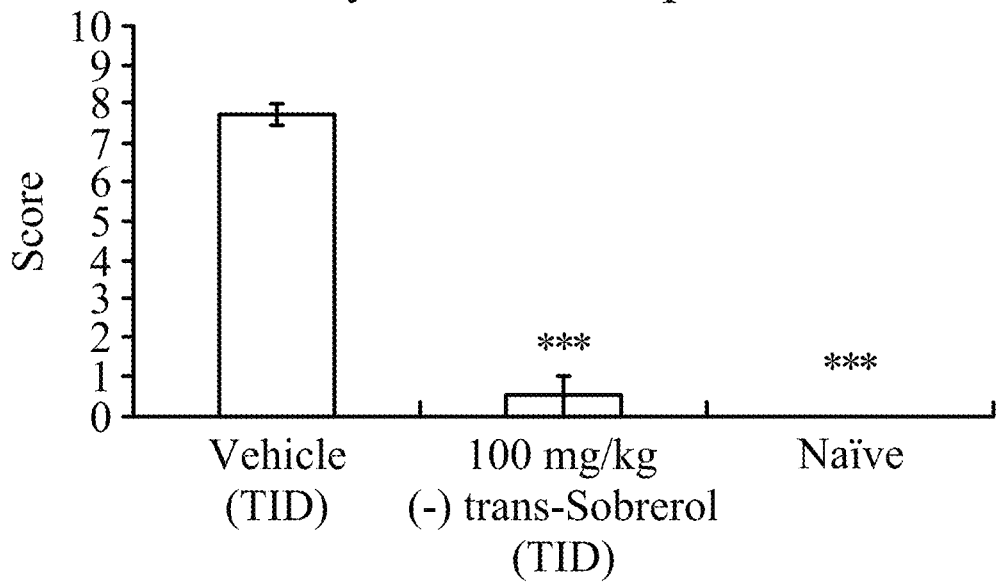
FIG. 7A shows demyelination scores of spinal cords of the mice with 100 mg/kg dosages of (−) trans-sobrerol three times a day, the mice treated with vehicle three times a day, and the mice without any treatment in a therapeutic administration experiment. TID (Ter in die): three times a day. Mean±standard error of the mean; n=10; ***: p<0.001, as compared to the vehicle treatment group. Student's t-test.
Figure 7B:
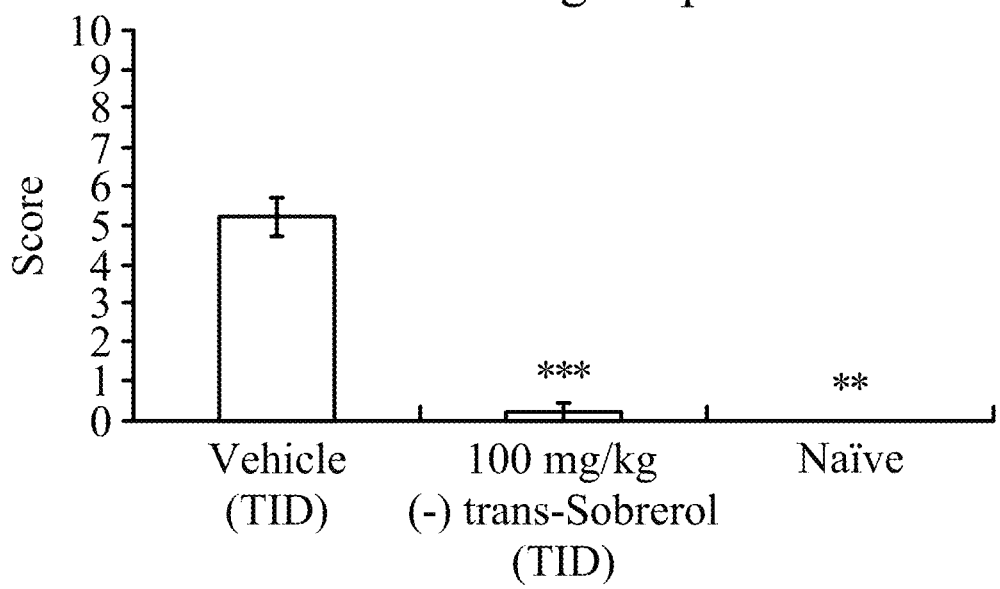
FIG. 7B shows axonal swelling scores of spinal cords of the mice with 100 mg/kg dosages of (−) trans-sobrerol three times a day, the mice treated with vehicle three times a day, and the mice without any treatment in a therapeutic administration experiment. TID (Ter in die): three times a day. Mean±standard error of the mean; n=10; : P<0.01, *: p<0.001, as compared to the vehicle treatment group. Student's t-test.
Figure 7C:
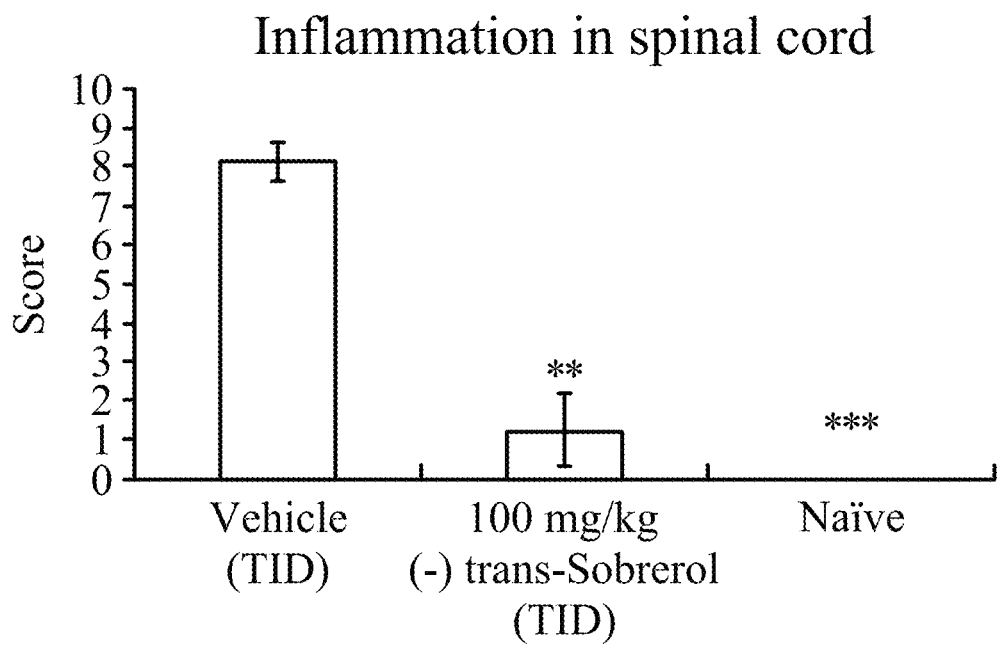
FIG. 7C shows inflammation scores of spinal cords of the mice with 100 mg/kg dosages of (−) trans-sobrerol three times a day, the mice treated with vehicle three times a day, and the mice without any treatment in a therapeutic administration experiment. TID (Ter in die): three times a day. Mean±standard error of the mean; n=10; : p<0.01, *: p<0.001, as compared to the vehicle treatment group. Student's t-test.
Figure 7D:
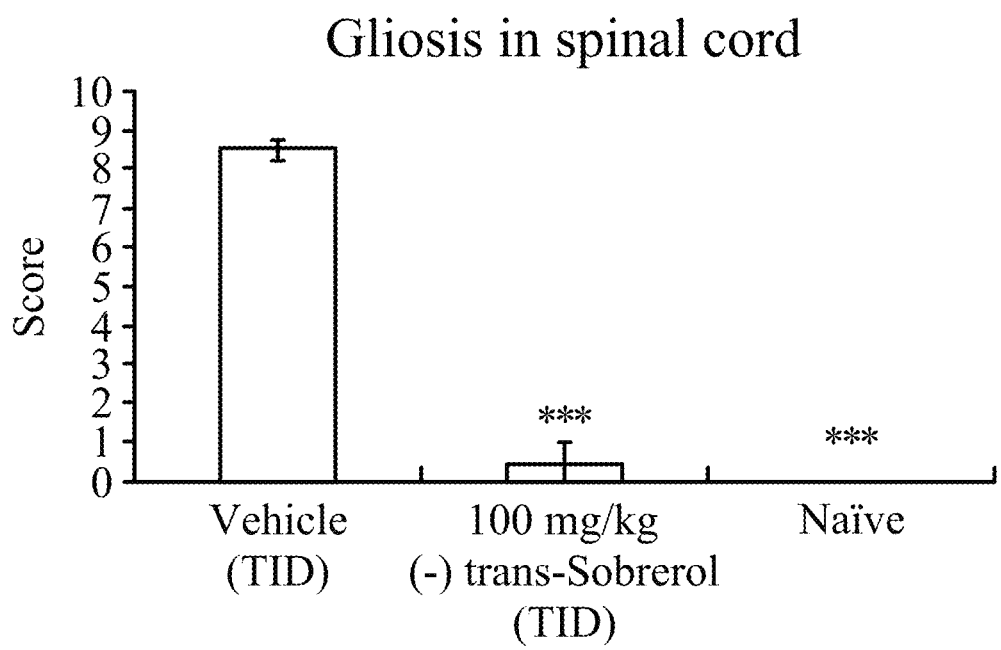
FIG. 7D shows gliosis scores of spinal cords of the mice with 100 mg/kg dosages of (−) trans-sobrerol three times a day, the mice treated with vehicle three times a day, and the mice without any treatment in a therapeutic administration experiment. TID (Ter in die): three times a day. Mean±standard error of the mean; n=10; ***: p<0.001, as compared to the vehicle treatment group. Student's t-test.

FIG. 7A shows demyelination scores of spinal cords of the mice with 100 mg/kg dosages of (−) trans-sobrerol three times a day, the mice treated with vehicle three times a day, and the mice without any treatment. FIG. 7B shows axonal swelling scores of spinal cords of the mice with 100 mg/kg dosages of (−) trans-sobrerol three times a day, the mice treated with vehicle three times a day, and the mice without any treatment. FIG. 7C shows inflammation scores of spinal cords of the mice with 100 mg/kg dosages of (−) trans-sobrerol three times a day, the mice treated with vehicle three times a day, and the mice without any treatment. FIG. 7D shows gliosis scores of spinal cords of the mice with 100 mg/kg dosages of (−) trans-sobrerol three times a day, the mice treated with vehicle three times a day, and the mice without any treatment.

Based on the results shown in FIGS. 6A-6D and FIGS. 7A-7D, it is clear that sobrerol is capable of effectively alleviating demyelination, inflammation, axonal swelling and gliosis in spinal cords of the EAE induced mice.

1-2. Administration of Mixture of (+) Trans-Sobrerol and (−) Trans-Sobrerol after Experimental Autoimmune Encephalomyelitis (EAE) Induction Mucoflux capsules containing a mixture of (+) trans-sobrerol and (−) trans-sobrerol were shucked and the powder in the capsules was dissolved in vehicle (DMSO:CrEL:saline=10:10:80) to form a solution of a mixture of (+) trans-sobrerol and (−) trans-sobrerol.

Based on method described in the section "3-1 Testing drug administration after experimental autoimmune encephalomyelitis (EAE) induction and clinical assessment" of "3. Therapeutic administration" of above "B. Methods", different doses of the mixture of (+) trans-sobrerol and (−) trans-sobrerol and vehicle (DMSO:CrEL:saline=10:10:80) were administered to the EAE induced mice by different dosing frequencies and then EAE scores of the mice were evaluated.

Figure 8A:
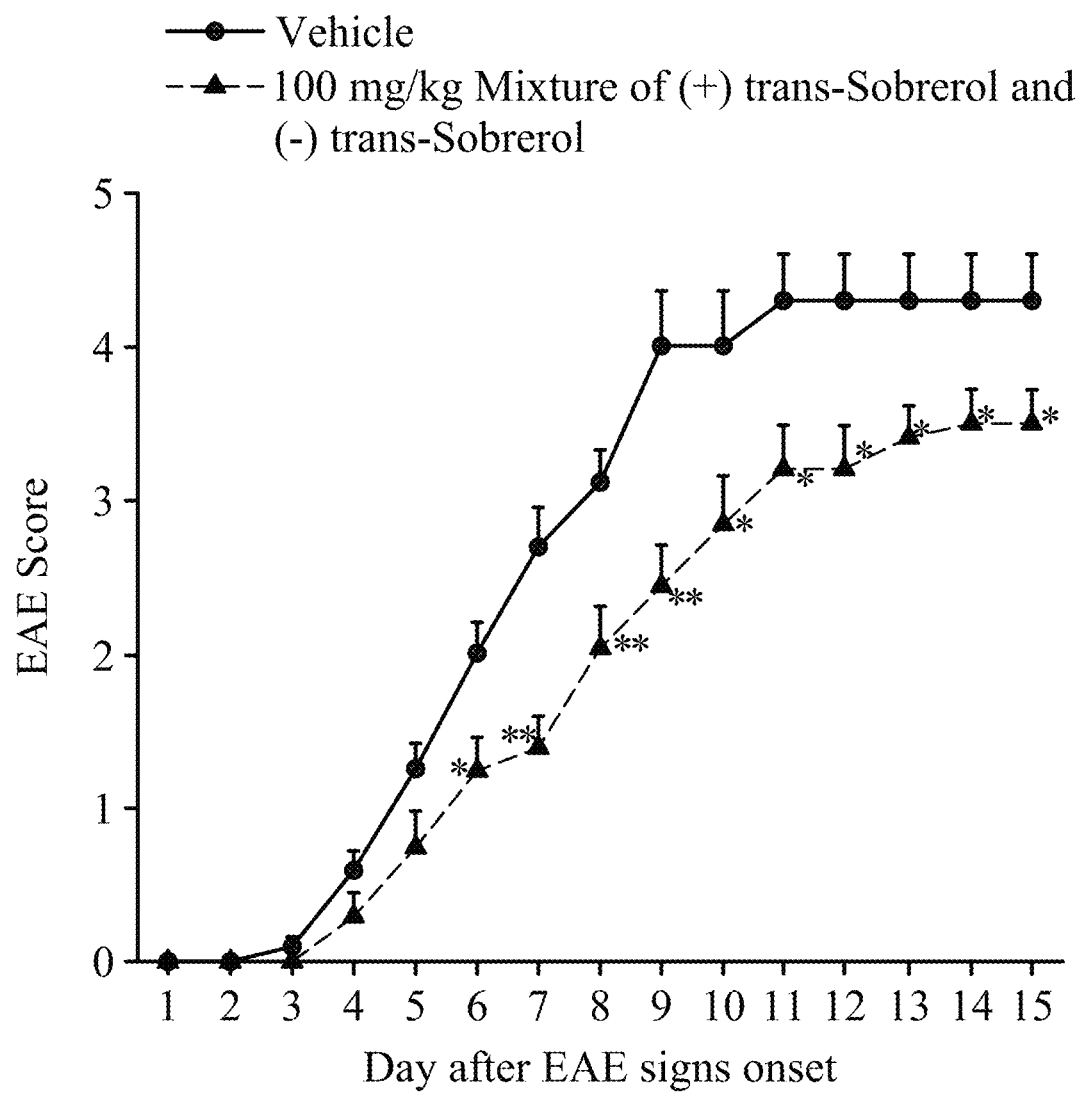
FIG. 8A shows respective EAE scores of the mice administered with 100 mg/kg dosage of the mixture of (+) trans-sobrerol and (−) trans-sobrerol and the mice administered with vehicle (DMSO:CrEL:saline=10:10:80), one time a day in a therapeutic administration experiment. Mean±standard error of the mean; n=10; *: p<0.05, **: p<0.01, as compared to the vehicle treatment group. Student's t-test.
Figure 8B:
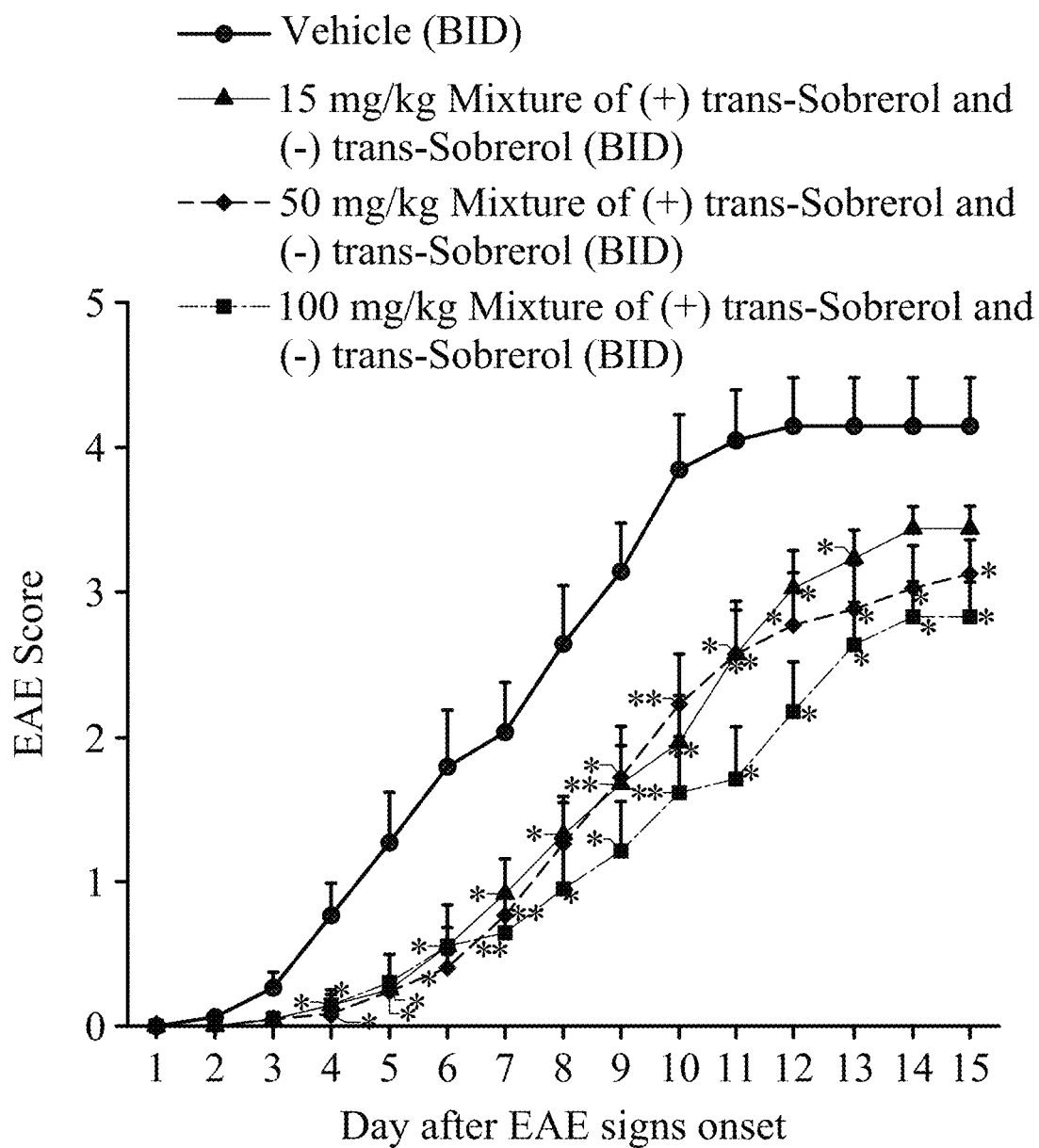
FIG. 8B shows respective EAE scores of the mice administered with 15 mg/kg, 50 mg/kg and 100 mg/kg dosages of the mixture of (+) trans-sobrerol and (−) trans-sobrerol and the mice administered with vehicle (DMSO:CrEL:saline=10:10:80), two times a day in a therapeutic administration experiment. BID (Bi in die): two times a day. Mean±standard error of the mean; n=10; *: p<0.05, **: p<0.01, as compared to the vehicle treatment group. Student's t-test.

The results are shown in FIGS. 8A and 8B. FIG. 8A shows respective EAE scores of the mice administered with 100 mg/kg dosage of the mixture of (+) trans-sobrerol and (−) trans-sobrerol and the mice administered with vehicle (DMSO:CrEL:saline=10:10:80), one time a day. FIG. 8B shows respective EAE scores of the mice administered with 15 mg/kg, 50 mg/kg and 100 mg/kg dosages of the mixture of (+) trans-sobrerol and (−) trans-sobrerol and the mice administered with vehicle (DMSO:CrEL:saline=10:10:80), two times a day.

According to the results shown in FIGS. 8A and 8B, it is clear that mixture of (+) trans-sobrerol and (−) trans-sobrerol can significantly alleviating symptoms of EAE in the EAE induced mice.

1-3. Administration of a Liquid Dosage Form of (−) Trans-Sobrerol after Experimental Autoimmune Encephalomyelitis (EAE) Induction Based on method described in the section "3-1 Testing drug administration after experimental autoimmune encephalomyelitis (EAE) induction and clinical assessment" of "3. Therapeutic administration" of above "B. Methods", different doses of the liquid dosage form of (−) trans-sobrerol prepared, (−) trans-sobrerol and vehicle (6% PEO-PPO-PEO and 40% 2-hydroxypropyl-beta cyclodextrin in water (%: mg/100 μl water)) were administered to the EAE induced mice by different dosing frequencies and then EAE scores of the mice were evaluated.

Figure 9A:
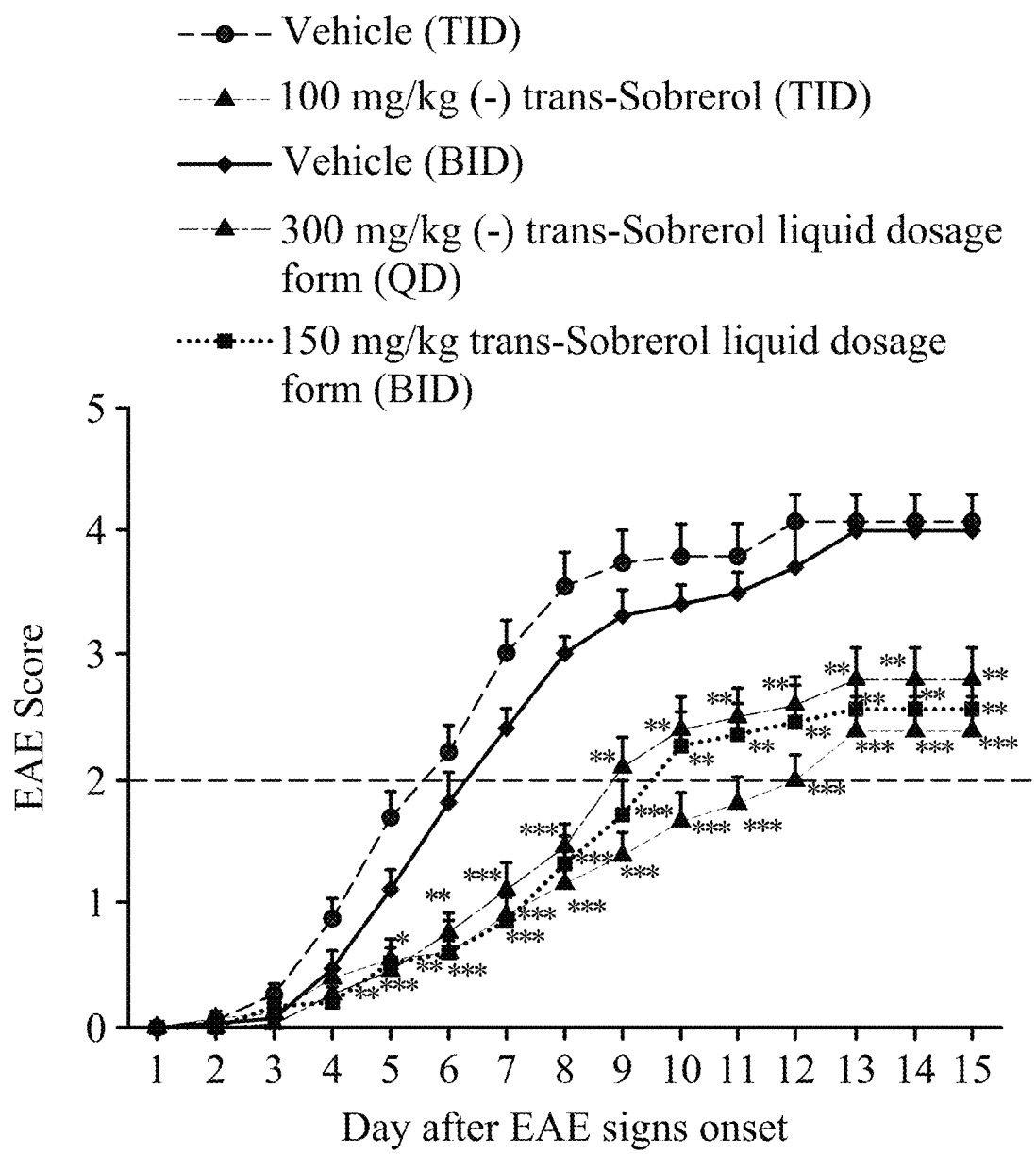
FIG. 9A shows respective EAE scores of the mice administered with 150 mg/kg dosage of the liquid dosage form of (−) trans-sobrerol prepared two times a day and 300 mg/kg dosage of the liquid dosage form of (−) trans-sobrerol prepared one time a day, the mice administered with 100 mg/kg dosage of (−) trans-sobrerol three times a day, and the mice administered with vehicle (6% PEO-PPO-PEO and 40% 2-hydroxypropyl-beta cyclodextrin (%: mg/100 μl water)) two times a day and vehicle (DMSO:CrEL:saline=10:10:80) three times a day in a therapeutic administration experiment. BID (Bi in die): two times a day; TID (Ter in die): three times a day; QD (quaque die): one time a day. Mean±standard error of the mean; n=10; *: p<0.05, : p<0.01, *: p<0.001, as compared to the vehicle treatment group. Student's t-test.
Figure 9B:
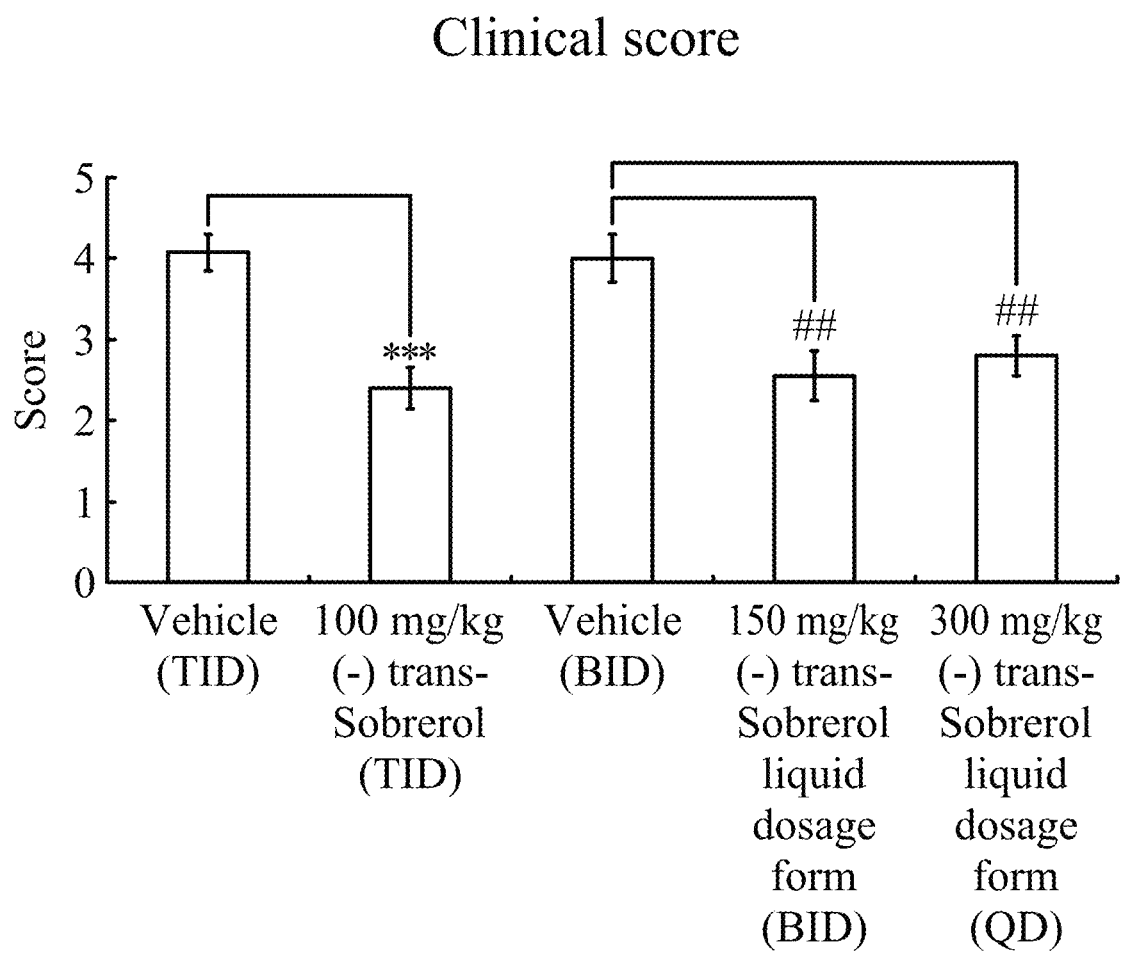
FIG. 9B shows respective EAE scores at Day 15 after EAE sings onset of the mice administered with 150 mg/kg dosage of the liquid dosage form of (−) trans-sobrerol prepared two times a day and 300 mg/kg dosage of the liquid dosage form of (−) trans-sobrerol prepared one time a day, the mice administered with 100 mg/kg dosage of (−) trans-sobrerol three times a day, and the mice administered with vehicle (6% PEO-PPO-PEO and 40% 2-hydroxypropyl-beta cyclodextrin (%: mg/100 μl water)) two times a day and vehicle (DMSO:CrEL:saline=10:10:80) three times a day in a therapeutic administration experiment. BID (Bi in die): two times a day; TID (Ter in die): three times a day; QD (quaque die): one time a day. Mean±standard error of the mean; n=10; ##: p<0.01, ***: p<0.001, as compared to the vehicle treatment group. Student's t-test

The results are shown in FIGS. 9A and 9B. FIG. 9A shows respective EAE scores of the mice administered with 150 mg/kg dosage of the liquid dosage form of (−) trans-sobrerol prepared two times a day and 300 mg/kg dosage of the liquid dosage form of (−) trans-sobrerol prepared one time a day, the mice administered with 100 mg/kg dosage of (−) trans-sobrerol three times a day, and the mice administered with vehicle (6% PEO-PPO-PEO and 40% 2-hydroxypropyl-beta cyclodextrin (%: mg/100 μl water)) two times a day and vehicle (DMSO:CrEL:saline=10:10:80) three times a day. FIG. 9B shows respective EAE scores at Day 15 after EAE sings onset of the mice administered with 150 mg/kg dosage of the liquid dosage form of (−) trans-sobrerol prepared two times a day and 300 mg/kg dosage of the liquid dosage form of (−) trans-sobrerol prepared one time a day, the mice administered with 100 mg/kg dosage of (−) trans-sobrerol three times a day, and the mice administered with vehicle (6% PEO-PPO-PEO and 40% 2-hydroxypropyl-beta cyclodextrin (%: mg/100 μl water)) two times a day and vehicle (DMSO:CrEL:saline=10:10:80) three times a day.

Based on the results shown in FIGS. 9A and 9B, it is clear that the effects of administration of the liquid dosage form of (−) trans-sobrerol prepared (300 mg/kg) by one time a day and (−) trans-sobrerol prepared (150 mg/kg) by two times a day are equivalent to that of administration of (−) trans-sobrerol (100 mg/kg) by three times a day. In other words, FIGS. 9A and 9B clear show that the liquid dosage form can reduce the dosing frequencies required by (−) trans-sobrerol.

2. Prophylaxis Administration Experiment 2-1. Administration of (−) Trans-Sobrerol Before Experimental Autoimmune Encephalomyelitis (EAE) Signs Onset (−) Trans-sobrerol was dissolved in vehicle (DMSO:CrEL:saline=10:10:80) to form a solution of (−) trans-sobrerol.

Based on method described in the section "4. Prophylaxis administration experiment" of above "B. Methods", administration of different doses of (−) trans-sobrerol and vehicle (DMSO:CrEL:saline=10:10:80) to the mice were started at day 7 after the experimental autoimmune encephalomyelitis (EAE) induction by different dosing frequencies and then EAE scores of the mice were evaluated.

Figure 10:
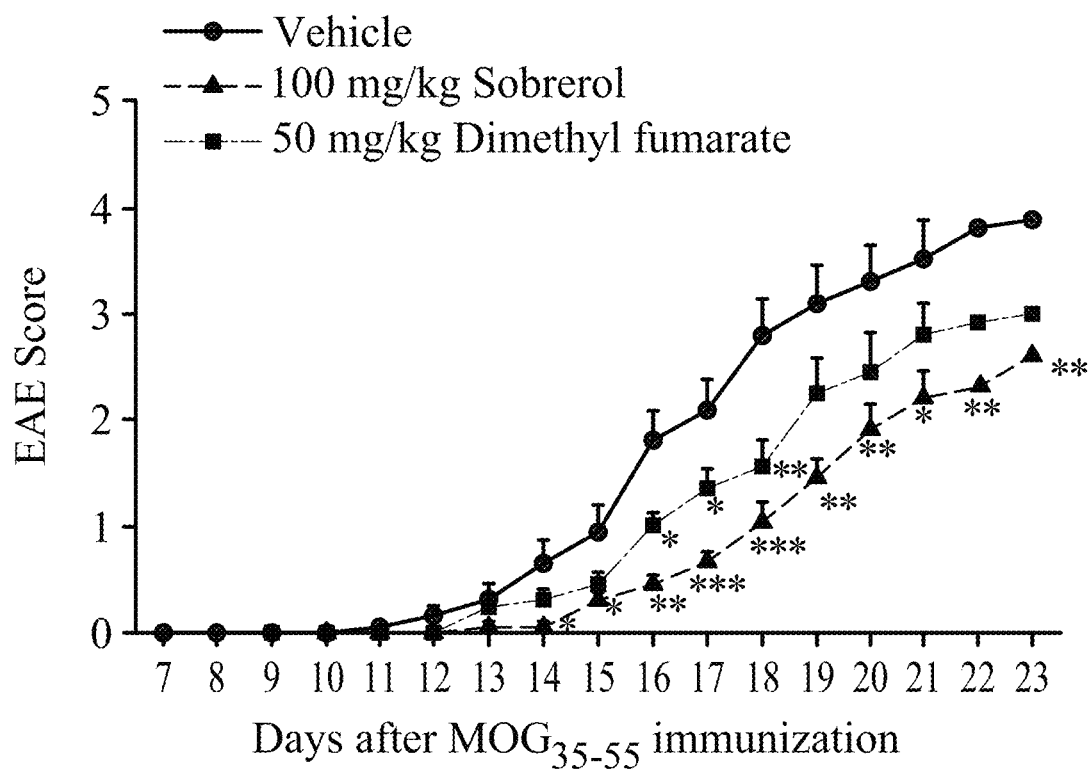
FIG. 10 shows respective EAE scores of the mice administered with 100 mg/kg dosages of (−) trans-sobrerol, the mice administered with vehicle (DMSO:CrEL:saline=10:10:80), and mice administered with 50 mg/kg dosages of dimethyl fumarate, onetime a day in a prophylaxis administration. Mean standard error of the mean; n=10; *: p<0.05, : p<0.01, *: p<0.001, as compared to the vehicle treatment group. Student's t-test.

The results are shown in FIG. 10. FIG. 10 shows respective EAE scores of the mice administered with 100 mg/kg dosages of (−) trans-sobrerol, the mice administered with vehicle (DMSO:CrEL:saline=10:10:80), and mice administered with 50 mg/kg dosages of dimethyl fumarate, one time a day.

According to the results shown in FIG. 10, it is clear that (−) trans-sobrerol can significantly alleviating symptoms of EAE in the EAE induced mice.

It will be apparent to those skilled in the art that various modifications and variations can be made to the disclosed embodiments. It is intended that the specification and examples be considered as exemplary only, with the true scope of the disclosure being indicated by the following claims and their equivalents.

The invention claimed is:

1. A method for treating an autoimmune neurological disease and/or a neurodegenerative disease, comprising:
administering an effective amount of at least one compound having Formula (I), Formula (II) or Formula (III), or its enantiomer, diastereomer or pharmaceutically acceptable salt to a subject in need thereof:

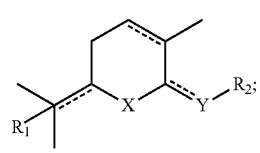

Formula (I)

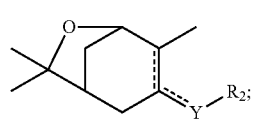

Formula (II)

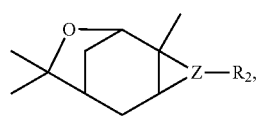

Formula (III)

wherein

═ is a single or double bond,

X is $NCH_3$ or $CH_2$,

Y is null, O or N,

Z is O or N, $R_1$ is H, OH, and $R_2$ is null, H, $C_1$-$C_8$ alkyl, —(C═O)-alkyl, —(C═O)-aryl, —(C═O)-alkyl-aryl, —(C═O)-heteroaryl, cycloalkyl or heterocycloalkyl, which optionally substituted by one or more of —OH, —$NO_2$, —$NH_2$, —$NR_3R_4$, carbonyl, alkoxyl, alkyl or —$OCF_3$, wherein $R_3$ and $R_4$ independently are H, alkyl, —$SO_2CH_3$, —(C═O)—$CH_3$ or —(C═O)—$NH_2$, wherein the at least one compound having Formula (I) comprises at least one compound having any one of Formula (IV) to Formula (XVI):

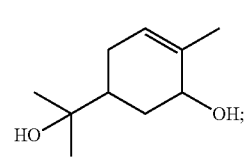

Formula (IV)

as trans-sobrerol

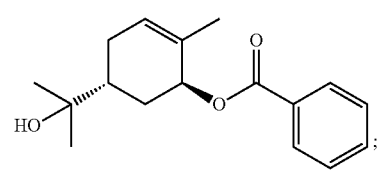

Formula (V)

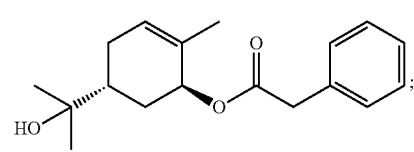

Formula (VI)

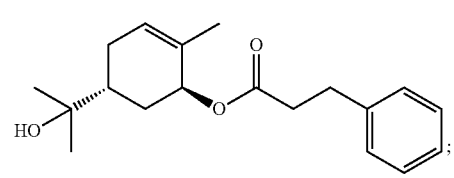

Formula (VII)

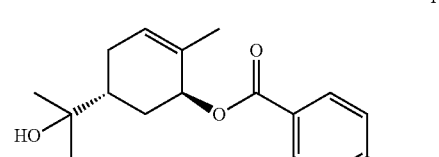

Formula (VIII)

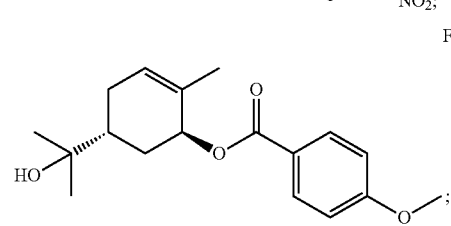

Formula (IX)

Formula (X)

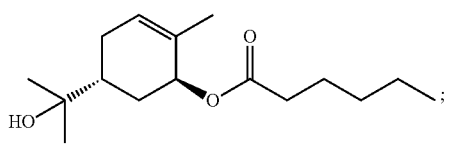

Formula (XI)

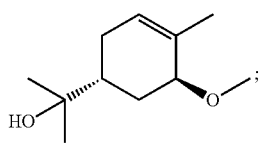

Formula (XII)

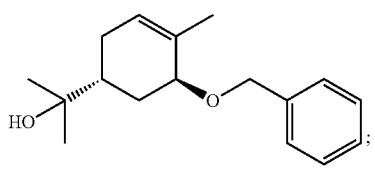

Formula (XIII)

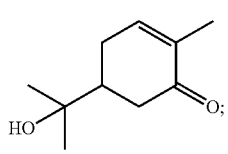

Formula (XIV)

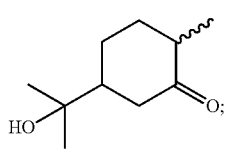

Formula (XV)

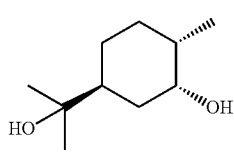

Formula (XVI)

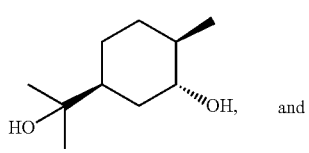 and wherein the at least one compound having Formula (II) comprises at least one compound having Formula (XVII):

Formula (XVII)

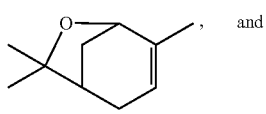, and wherein the at least one compound having Formula (III) comprises at least one compound having Formula (XVIII):

Formula (XVIII)

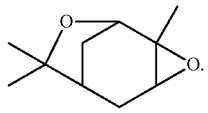

2. The method for treating an autoimmune neurological disease and/or a neurodegenerative disease as claimed in claim 1, wherein the at least one compound having Formula (I), Formula (II) or Formula (III), or its enantiomer, diastereomer or pharmaceutically acceptable salt is the at least one compound having Formula (I).

3. The method for treating an autoimmune neurological disease and/or a neurodegenerative disease as claimed in claim 2, wherein the at least one compound having Formula (I) is at least one compound having Formula (IV) as trans-sobrerol:

Formula (IV)

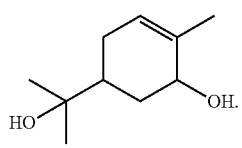

4. The method for treating an autoimmune neurological disease and/or a neurodegenerative disease as claimed in claim 3, wherein the trans-sobrerol comprises (+) trans-sobrerol, (−) trans-sobrerol or a combination thereof.

5. The method for treating an autoimmune neurological disease and/or a neurodegenerative disease as claimed in claim 4, wherein the trans-sobrerol is (+) trans-sobrerol.

6. The method for treating an autoimmune neurological disease and/or a neurodegenerative disease as claimed in claim 4, wherein the trans-sobrerol is (−) trans-sobrerol.

7. The method for treating an autoimmune neurological disease and/or a neurodegenerative disease as claimed in claim 4, wherein the trans-sobrerol is a mixture of (+) trans-sobrerol and (−) trans-sobrerol.

8. The method for treating an autoimmune neurological disease and/or a neurodegenerative disease as claimed in claim 1, wherein the autoimmune neurological disease comprises multiple sclerosis, Neuromyelitis optica, Lambert-Eaton myasthenic syndrome, autoimmune inner ear disease, narcolepsy, neuromyotonia, Guillain-Barre syndrome, myasthenia gravis, systemic lupus erythematosus, transverse myelitis or acute disseminated encephalomyelitis.

9. The method for treating an autoimmune neurological disease and/or a neurodegenerative disease as claimed in claim 1, wherein the neurodegenerative disease comprises Alzheimer's disease, Huntington's disease, Parkinson's disease, Schizophrenia, depression, Amyotrophic lateral sclerosis, multi-infarct dementia, Motor neuron disease or neurofibromatosis.

* * * * *